United States Patent
Gandola et al.

(10) Patent No.: US 11,904,074 B2
(45) Date of Patent: Feb. 20, 2024

(54) DEVICES AND METHODS FOR CONTACTING LIVING TISSUE

(71) Applicant: ISL, LLC, Woodland Hills, CA (US)

(72) Inventors: Kent R. Gandola, San Diego, CA (US); Jerome K. Aarestad, Escondido, CA (US)

(73) Assignee: ISL, LLC, Woodland Hills, CA (US)

( * ) Notice: Subject to any disclaimer, the term of this patent is extended or adjusted under 35 U.S.C. 154(b) by 823 days.

(21) Appl. No.: 16/646,895

(22) PCT Filed: Sep. 12, 2018

(86) PCT No.: PCT/US2018/050693
§ 371 (c)(1),
(2) Date: Mar. 12, 2020

(87) PCT Pub. No.: WO2019/055531
PCT Pub. Date: Mar. 21, 2019

(65) Prior Publication Data
US 2020/0276364 A1 Sep. 3, 2020

Related U.S. Application Data

(60) Provisional application No. 62/700,141, filed on Jul. 18, 2018, provisional application No. 62/557,587, filed on Sep. 12, 2017.

(51) Int. Cl.
*A61L 31/14* (2006.01)
*A61M 16/06* (2006.01)
(Continued)

(52) U.S. Cl.
CPC ............ *A61L 31/146* (2013.01); *A61F 11/08* (2013.01); *A61L 27/165* (2013.01); *A61L 27/507* (2013.01);
(Continued)

(58) Field of Classification Search
CPC ..... A61L 31/146; A61H 9/0057; A61M 16/06
See application file for complete search history.

(56) References Cited

U.S. PATENT DOCUMENTS 4,073,776 A 2/1978 Galkiewicz et al.
5,343,878 A 9/1994 Scarberry et al.
(Continued)

FOREIGN PATENT DOCUMENTS

EP 2338415 A1 6/2011
GB 2493520 A 2/2013
(Continued)

OTHER PUBLICATIONS

Office Action issued by the JPO in Japanese Patent Application No. 2020-536729 dated May 17, 2022—incl Engl lang transl (14 pages total).
(Continued)

*Primary Examiner* — Dah-Wei D. Yuan
*Assistant Examiner* — Andrew J Bowman
(74) *Attorney, Agent, or Firm* — Acuity Law Group, P C; Michael A. Whittaker

(57) ABSTRACT

The present invention provides materials and methods for forming an interface between an appliance and living tissue using a foamed elastomeric material which contacts the tissue or similar surfaces. The elastomeric material is in the form of a durable and washable material that when applied to living tissue or similar surfaces displaces and flows in to non-conforming areas creating an air and/or water tight seal that substantially returns to an original shape when removed from the contact surface. The appliance may also include structural elements designed to optimize comfort, compliance and seal achieved through minimizing the pressure variation along the contact surface of the therapy device.

17 Claims, 4 Drawing Sheets

(51) Int. Cl.
    *A61F 11/08*     (2006.01)
    *A61L 27/16*     (2006.01)
    *A61L 27/50*     (2006.01)
    *A61L 27/56*     (2006.01)
    *A61L 29/04*     (2006.01)
    *A61L 29/14*     (2006.01)
    *A61L 31/04*     (2006.01)
    *A63B 33/00*     (2006.01)
    *B63C 11/12*     (2006.01)
    *C08J 9/14*     (2006.01)
    *H04R 1/10*     (2006.01)

(52) U.S. Cl.
    CPC ............ *A61L 27/56* (2013.01); *A61L 29/042* (2013.01); *A61L 29/146* (2013.01); *A61L 31/049* (2013.01); *A61M 16/0622* (2014.02); *A61M 16/0666* (2013.01); *A63B 33/002* (2013.01); *B63C 11/12* (2013.01); *C08J 9/142* (2013.01); *H04R 1/10* (2013.01); *A61L 2300/404* (2013.01); *C08J 2383/04* (2013.01)

(56) References Cited

U.S. PATENT DOCUMENTS

| | | | |
|---|---|---|---|
| 5,436,274 | A | 7/1995 | Sumpter et al. |
| 6,022,904 | A | 2/2000 | Soellradl et al. |
| 7,182,082 | B2 | 2/2007 | Hoffrichter |
| 7,393,879 | B1 | 7/2008 | Kresta et al. |
| 7,762,263 | B2 | 7/2010 | Aarestad et al. |
| 7,772,345 | B2 | 8/2010 | Banach et al. |
| 8,173,717 | B2 | 5/2012 | Jacobs et al. |
| 8,410,239 | B2 | 4/2013 | Blanc et al. |
| 9,820,881 | B2 | 11/2017 | Aarestad et al. |
| 2002/0157163 | A1* | 10/2002 | Chen ............... G06F 3/039 2/16 |
| 2005/0086914 | A1 | 4/2005 | Fennelly |
| 2005/0267321 | A1 | 12/2005 | Shadduck |
| 2006/0079823 | A1* | 4/2006 | Utterberg ........ A61F 13/0246 602/53 |
| 2010/0018534 | A1* | 1/2010 | Veliss ............ A61M 16/0622 128/206.24 |
| 2010/0298778 | A1 | 11/2010 | Bracken et al. |
| 2011/0054409 | A1 | 3/2011 | Nishtala |
| 2011/0066086 | A1 | 3/2011 | Aarestad et al. |
| 2011/0218258 | A1 | 9/2011 | Frericks et al. |
| 2011/0282444 | A1 | 11/2011 | Liu et al. |
| 2012/0108889 | A1 | 5/2012 | Behan |
| 2013/0053175 | A1 | 2/2013 | Shiga et al. |
| 2014/0024730 | A1 | 1/2014 | Shimakawa |
| 2014/0128491 | A1 | 5/2014 | Hayashi |
| 2014/0144450 | A1 | 5/2014 | Aarestad et al. |
| 2015/0314099 | A1 | 11/2015 | Carroll et al. |
| 2015/0348518 | A1 | 12/2015 | Kear |
| 2017/0361048 | A1 | 12/2017 | Moiler et al. |

FOREIGN PATENT DOCUMENTS

| | | | |
|---|---|---|---|
| JP | H03100649 U | 10/1991 | |
| JP | H05041567 U | 6/1993 | |
| JP | 2005212632 A | 8/2005 | |
| JP | 2006297935 A | 11/2006 | |
| JP | 2011525829 A | 9/2011 | |
| WO | WO-2009143586 A1 * | 12/2009 | ............ A61M 16/06 |
| WO | 2016000040 A1 | 1/2016 | |
| WO | 2019055531 A1 | 3/2019 | |

OTHER PUBLICATIONS

Extended European Search Report issued by EPO in European Application No. 20769086 dated Oct. 18, 2022 (8 pages).

Extended European Search Report and Written Opinion issued in PCT/US2018/050693 dated Sep. 2, 2021.

Reddy et al., Model experiments to study the stress distributions in a seated buttock. J Biomech. 1982; 15(7):493-504.

International Search Report and Written Opinion issued in PCT/US2018/050693 dated Dec. 4, 2018.

International Preliminary Report on Patentability issued in PCT/US2018/050693 dated Mar. 17, 2020.

Partial Supplementary European Search Report issued in EP 18856561 dated Apr. 26, 2021.

* cited by examiner

DEVICES AND METHODS FOR CONTACTING LIVING TISSUE

The present invention is filed under 35 U.S.C. § 371 as the U.S. national phase of International Application No. PCT/US2018/050693, filed Sep. 12, 2018, which designated the U.S. and claims the benefit of U.S. Provisional Application No. 62/557,587, filed Sep. 12, 2017, and of U.S. Provisional Application No. 62/700,141, filed Jul. 18, 2018, each of which is hereby incorporated by reference in its entirety including all tables, figures, and claims and from each of which priority is claimed.

BACKGROUND OF THE INVENTION

The following discussion of the background of the invention is merely provided to aid the reader in understanding the invention and is not admitted to describe or constitute prior art to the present invention.

U.S. Pat. Nos. 5,343,878, 7,182,082, and 7,762,263 describe various devices which purport to utilize application of negative pressure upon the external neck surface of patients. A therapeutic appliance is typically provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage. In certain embodiments, these appliances can provide a chamber (e.g., a hollow space filled with air molecules) lying between the interior surface of the chamber and the throat. The therapy appliance is operably connected to a vacuum source which is configured to produce a partial negative pressure in this chamber. Application of a therapeutic level of negative pressure in the chamber elicits movement of the upper airway and may alleviate conditions such as snoring, sleep apnea, and full or partial airway collapse whether during sleep or when a patient is undergoing a medical procedure while under sedation for example.

It can be difficult to obtain a proper and comfortable fit between such an apparatus and the patient to create and maintain the differential negative pressure (relative to atmospheric pressure for example) at the desired location on the patient. In the case of devices intended for daily wear for many hours, any points of high contact pressure from the device's sealing on the user's tissue soon become too uncomfortable for continued use. Further, success of these negative pressure therapies can be determined by a device's ability to accommodate (flex, bend, flow, etc.) varying anatomical features (i.e. device compliance). User compliance with therapy is maximized by a good comfortable interface between the device and the user, and by an interface that minimizes or eliminates tell-tale post-treatment red marks when the device is removed. Finally, the device should optimally accommodate some stubble growth and/or movement to different sleeping positions without loss of seal.

Similarly, masks adapted for infusion of a fluid, e.g., gas, to a patient, in particular those suffering from obstructive sleep apnea (OSA), are preferably designed to not only deliver the fluid, but also to seal well on the patient's face, to be adaptable with any patient movement, and to be comfortable. Masks that are comfortable and compliant but do not seal optimally are less effective. If the frame for the mask is hard plastic, sealing and compliance must be provided by the facial cushion. A very sensitive area of the face where seal is usually located is the nasal bridge region. Any increase in pressure may be directly translated to the nasal bridge region, resulting in a fit that is uncomfortable and even painful. Some masks had flowable-type gels at the skin interface which were heavy and when the membrane was worn could rupture and leak gel into the airways, creating a potential health hazard.

While an enclosed gel is a good absorber of pressure (e.g., areas of high contact pressure may be redistributed), it is not necessarily a good sealing medium, particularly when it lacks "compliance" (e.g., by not being able to remain in intimate contact with the patient's skin due to minor relative movement, such as experienced by natural body movement). Compliance is the level of displacement achievable between the patient's face and cushion and/or the mask's ability to maintain a comfortable seal. ResMed's Activa™ cushion is an example of a cushion providing very good compliance. The lack of compliance and resilience may affect seal performance and may create localized pressure points such as on higher facial landmarks, especially the nasal bridge region.

Likewise, Filtering Face-piece Respirators (FFRs) play a critical role in everyday life. They are available for purchase to the general public in most hardware stores and are recommended, or required, for use in a wide variety of home, public, and occupational environments-especially in healthcare settings. Their principal function is to provide respiratory protection against both non-biological and biological particulates.

In practice, FFRs are used generally to protect the wearer. In healthcare institutions, and public health settings, however, FFRs must function both to protect the wearer from potentially harmful particulate matter, including biological pathogens, and/or to protect patients and others from the wearer exhaling pathogens into the environment. During surgical procedures, for example, the smoke plume generated from electrosurgical use has been shown to contain a wide variety of vaporized viral organisms capable of infection, including HIV and Human Papilloma Virus (HPV). A FFR in such a setting must therefore protect the surgeon and those in the operating room, while at the same time protecting the patient from the surgeon's exhaled pathogens coming into contact with the surgical field.

With respect to sealing the mask to the wearer's face, the principal reason to achieve such a seal is to avoid leakage around the filter portion of the mask, as opposed to through the filter. This is true for both inhaled and/or exhaled particulate matter coming from the user. Face Seal Inner Leakage (FSIL) as well as Face Seal Outer Leakage (FSOL), (collectively referred to as Face Seal Leakage (FSL)) is difficult to reduce because of the significant variances in human facial anatomy. Anthropometric studies have revealed the substantial differences in the multiple variables of human facial anatomy. These are notable, perhaps not coincidentally, in the three areas that are common for face seal leakage to occur: 1) the nasal bridge and the cheek bone, 2) the cheek bone to the edge of the lower jaw, and 3) around and under the area between the undersurface of the chin back toward the angle of the jaw. The problem of face seal leakage may also be compounded by FFRs being made in fairly generic "small, medium, and large" sizes, and often simply as a "one size fits all" design.

BRIEF DESCRIPTION OF THE INVENTION

It is an object of the invention to provide an appliance designed to be contacted with living tissue, where a tissue interface region of the appliance is adapted to form a conforming seal between the appliance and the tissue. In certain aspects, the appliance is configured to attach and seal to a patient's external or internal tissue, such as a face, a neck, an area surrounding a wound, etc.

As described hereinafter, the tissue interface region may comprise an inherent sticky or adhesive quality (referred to as "tack") to improve the sealing, resist sliding against tissue, and increase the breadth of anatomical differences that the therapy device will accommodate to secure an appropriate seal and or fit.

In a first aspect, the invention provides an appliance configured to contact animal, preferably mammalian, and most preferably human, tissue, comprising:

(a) a tissue interface portion comprising a viscoelastic foam configured to provide a tissue contact surface of the appliance, wherein the viscoelastic foam comprises one or more of the following properties:

a Shore A of about 0 or less, and preferably a Shore 00 durometer of about 30 or less, more preferably of about 20 or less, and still more preferably of about 10 or less, in each case as measured using the Standard Test Method for Rubber Property—Durometer Hardness ASTM D2240-15;

a density (specific gravity) of about 0.9 g/cm$^3$ or less; and/or a level of tack measured using the Standard Test Method for Pressure-Sensitive Tack of Adhesives ASTM D2979-16 of about 9 mJ/cm$^2$ or less, preferably about 7 mJ/cm$^2$ or less, most preferably about 5 mJ/cm$^2$ or less;

an elastic (storage) modulus of between about 0.3 kPa to about 30 kPa, and preferably between about 1 kPa and about 15 kPa;

a viscous (loss) modulus of between about 0.4 kPa to about 7 kPa, and preferably between about 0.8 kPa and about 7 kPa; and (b) a non-contacting portion configured to support the tissue interface portion and to be separated from the tissue by the tissue interface portion.

The term "viscoelastic" as used herein refers to materials that exhibit both viscous and elastic characteristics when undergoing deformation. Unlike purely elastic substances, a viscoelastic substance has an elastic component and a viscous component. The viscosity of a viscoelastic substance gives the substance a strain rate dependence on time. Purely elastic materials do not dissipate energy (heat) when a load is applied, then removed. However, a viscoelastic substance loses energy when a load is applied, then removed.

The storage and loss modulus in viscoelastic materials measure the stored energy, representing the elastic portion, and the energy dissipated as heat, representing the viscous portion. The storage (E') and loss (E') moduli are measured in KPa using Dynamic Mechanical Analysis (DMA) methods known in the art. In certain embodiments, the viscoelastic foam comprises one or both of an elastic (storage) modulus of between about 10 kPa and about 15 kPa and a viscous (loss) modulus of between about 2 kPa and about 7 kPa.

The term "tissue" as used herein refers to a collection of cells. Tissue can include, and in some embodiments preferably includes, cells that grow and/or reproduce. Tissue can comprise a layer of cells that are not living, such as skin which comprises a stratum corneum layer overlying the living cells of the tissue. Tissue is preferably a part of a mammalian, and most preferably human, body.

In certain embodiments, the viscoelastic foam exhibits a Shore A durometer of about 10 or less, preferably about 5 or less, and still more preferably about 1 or less; or a Shore 00 durometer of about 30 or less, more preferably of about 20 or less, and still more preferably of about 10 or less; or a Shore 000 durometer of 50 or less, and most preferably 30 or less.

In certain embodiments, the viscoelastic foam exhibits a tack measured using the Standard Test Method for Pressure-Sensitive Tack of Adhesives ASTM D2979-16 of at least 0.1 mJ/cm$^2$, preferably at least 0.3 mJ/cm$^2$, and most preferably at least 0.5 mJ/cm$^2$. Thus, in various embodiments, the tack is between 0.1 and 9 mJ/cm$^2$, between 0.3 and 7 mJ/cm$^2$, and between 0.5 and 5 mJ/cm$^2$.

By "inherent tack" is meant that the viscoelastic foam material is itself tacky, as opposed to having a tacky material added to a surface of the foam after the production of the foam.

In certain embodiments, the viscoelastic foam may comprise or consist of a foamed silicone rubber, such as a high consistency rubber ("HCR") or a liquid silicone rubber ("LSR"). Such a viscoelastic foam may be formed from silicone rubber and foaming agent blended together and cured to produce a compliant, durable human interface layer. The viscoelastic foam may be provided as a single layer, or may be a component of a lamination stack of materials positioned on all or a portion of the tissue interface portion of the appliance. In the case of a lamination stack, the viscoelastic foam preferably provides the outermost layer (and hence provides the tissue contact layer) of the lamination stack.

In certain embodiments, the viscoelastic foam may comprise a tackifier added during production of the foam. Tackifiers are chemical compounds used in formulating elastomers to increase the tack, the stickiness of the surface of the adhesive. See, e.g., U.S. Pat. Nos. 4,073,776; and 7,772,345. Tackifiers tend to have low molecular weight, and glass transition and softening temperature above room temperature, providing them with suitable viscoelastic properties. Tackifiers can comprise up to about 40% of total mass. Examples of tackifiers include rosins and their derivatives, terpenes and modified terpenes, aliphatic, cycloaliphatic and aromatic resins (C5 aliphatic resins, C9 aromatic resins, and C5/C9 aliphatic/aromatic resins), hydrogenated hydrocarbon resins, and their mixtures, terpene-phenol resins (TPR, used often with ethylene-vinyl acetate adhesives)). Silicone rubber-based pressure-sensitive adhesives may utilize special tackifiers based on "MQ" silicate resins, composed typically of a monofunctional trimethyl silane ("M") reacted with quadrafunctional silicon tetrachloride or silicone tetroxide ("Q"). In certain embodiments, the viscoelastic foam does not include a tackifier or an adhesive.

While tackifiers may find use in the present invention, in preferred embodiments the viscoelastic foam does not comprise tackifiers or an adhesive, and the tack quality is an inherent property of the elastomer itself.

In certain embodiments, the viscoelastic foam is formed using a silicone base, a foaming agent, and a catalyst. An example of such a foaming agent is an ammonium, sodium, or potassium salt, however a variety of commercially available chemical foaming agents are known in the art. Typically, these foaming agents liberate a gas (e.g., $N_2$, $CO_2$) during the foaming process. A catalyst may be selected from the group consisting of an iron catalyst, a cobalt catalyst, a zinc catalyst, a titanate catalyst, a tin catalyst, a platinum catalyst, or an acid catalyst.

While it is preferred that the entire tissue interface portion of the appliance comprise the viscoelastic foam, in certain embodiments only portions of the tissue interface portion comprises the viscoelastic foam. In certain embodiments, the viscoelastic foam may be one or a multiplicity of continuous or discontinuous concentric annular rings, either abutting or having some pitch separation between them. In other embodiments, the viscoelastic foam may be one or a multiplicity of connected or discontinuous spiral rings, either abutting or having some pitch separation between them.

The percentage by weight of the foaming agent additive to the elastomeric component (e.g., a silicone rubber) will preferably be 1 to 10%, and more preferably 1 to 5%, and most preferably 1.5 to 3%. In various embodiments, the viscoelastic foamed material will be applied onto the appliance and cured in such a manner as to cause the viscoelastic foamed material to "skin-over," providing a smooth closed cell surface at the tissue contact surface of the viscoelastic foamed material that helps to mitigate potential leakage around the interface seal.

In certain embodiments, the viscoelastic foam comprises a reinforcing filler such as silica, silica aerogel, silica xerogel, titanium dioxide, diatomaceous earth, iron oxide, aluminum oxide, zinc oxide, quartz, calcium, carbonate, magnesium oxide, carbon black, graphite, glass fibers, glass micro spheres, glass micro balloons, glass beads, carbon fibers, silicon carbide, polystyrene beads, microcrystalline cellulose, nanoparticles such as carbon nanotubes, layered silicate etc., and metal fibers.

In certain embodiments, the viscoelastic foam comprises an antimicrobial additive with active ingredients such as a silver, silver ions, silver ions encapsulated in a glass particle, silver sodium zirconium hydrogenphosphate, 3-(Trimethoxysilyl)propyl dimethyl octadecyl ammonium chloride, benzalkonium chloride, polyhexamethylenebiguanide (PHMB), etc., that retard or prevent the growth of microbes such as bacteria, fungi, and viruses. Some of these may be supplied in the form of inorganic compounds and may comprise either micro-sized (>100 nm) or nano-sized (<100 nm) particles.

In certain embodiments, the sealing element may comprise a tacky material inherent in, or positioned on, all or a portion of the contact area. By way of example only, the tacky material can comprise either a room-temperature vulcanizing or a heat-curing silicone rubber. The tacky material may be a single layer, or may be a component of a lamination stack of materials positioned on all or a portion of the contact area.

In certain embodiments, the viscoelastic foam provides a fluidly sealed surface.

While foaming and cure of a viscoelastic foam may take place at room temperature, in certain embodiments, the viscoelastic foam is cured at a temperature of at least between about 50° C. and 60° C., more preferably at least about 120° C., still more preferably at least about 150° C., and yet more preferably at least about 170° C.

Examples of silicone foams and processes to make them may be found, for example, in U.S. Pat. Nos. 8,410,239; 8,173,717; 7,393,879; 6,022,904; and 5,436,274, each of which is hereby incorporated by reference in its entirety. In certain embodiments, curing takes place at a temperature between about 100° C. and about 250° C.

In certain embodiments, the viscoelastic foam has a density of 0.9 g/cm$^3$ or less, more preferably 0.8 g/cm$^3$ or less, still more preferably 0.7 g/cm$^3$ or less, and most preferably 0.5 g/cm$^3$ or less.

In various embodiments, the appliance may be an eye protection mask, a scuba mask, swim goggles, a medical appliance, a breathing mask, a negative pressure chamber configured to cover a portion of the body such as a negative-pressure wound therapy device or a continuous negative external pressure (cNEP) therapy device, headphones, ear plugs, earphones, or the like.

As described hereinafter, the appliance described herein is suited for providing a pressure containment structure in the form of a sealed chamber that is configured to administer negative, neutral or positive pressure to a targeted therapy area on the external or internal tissue of an individual.

The term "pressure containment structure," as used herein refers to the elements of the therapy device that contain a negative pressure, positive or neutral pressure during use. The pressure containment structure may comprise a rigid, semi-rigid, or flexible membrane that defines a dome-like chamber element, an aperture in the pressure containment structure through which a vacuum source may be affixed or applied through, and a sealing element affixed to the dome-like chamber that forms the tissue interface portion between the chamber element and the individual.

Such a pressure containment structure may be used to create a pressure differential between an interior space formed by the appliance when mated to living tissue (e.g., a location on a human), and the exterior atmospheric pressure. Preferably, the viscoelastic foam creates a seal to the tissue that maintains the pressure differential. A certain amount of leakage at the seal may be tolerated so long as the desired pressure differential can be achieved and maintained. Preferably, the leakage is no more than between about 0.008 ml/min and about 8 ml/min, and most preferably between about 0.1 ml/min and about 1.6 ml/min. In the case of an eye mask for use in water (e.g., a SCUBA mask), the viscoelastic foam is preferably fluidly sealed to seawater such that a pressure differential of about 1 atm leaks no more than 10% of the internal volume, and preferably 5% of the internal volume or less, in 10 minutes, 20 minutes, or most preferably 30 minutes.

In certain embodiments, the appliance may be configured to provide an approximately constant and evenly distributed contact pressure across the entire tissue interface portion when the appliance is mated to the individual and a therapeutic level of pressure (either positive or negative) is applied within the appliance. In the case of a negative pressure appliance, this approximate contact pressure may range from 0.9 to 1.5 times, and preferably be about 1.1 to 1.3 times, the negative pressure within the therapy device.

In certain embodiments, when the therapy device is mated to the individual and a therapeutic level of negative pressure is applied within the chamber, the approximate contact pressure applied to the tissue surface is approximately 1.2 times the negative pressure within the chamber. In various embodiments, a therapy device designed to maintain a neutral or positive pressure within the chamber could also be configured to distribute a constant and even contact pressure.

In related aspects, the present invention relates to methods of applying negative pressure therapy to an individual in need thereof, comprising mating a therapy device as described herein to the individual, and applying a therapeutic level of negative pressure within the chamber, thereby increasing patency of the airway of the individual. Such methods can be for treatment of sleep apnea; for treatment of snoring; for treatment of full or partial upper airway collapse, whether during sleep or during medical procedures requiring some level of sedation; for treatment of full or partial upper airway obstruction; for negative pressure treatment of a wound caused by, for example an injury or a surgery; etc.

The terms "external area" and "external surface" of an individual as used herein refers to a portion of the external tissue surface of the individual. The terms "internal area" and "internal surface" of an individual as used herein refers to a portion of the internal surface or partially internal surface of the individual. For example, in various embodiments, the therapy device may be configured to be applied to and seal sites of ostomies or wounds or to sealing around laryngeal tubes in the airway. In various embodiments, the therapy device is configured to provide optimized fitting parameters, for example, seal, comfort and local device compliance throughout all points of contact. This may be achieved by minimizing the contact pressure differential from one point of contact on the tissue of a patient to another through design features of the compliant conforming interface and design features of the sealed chamber element of a negative pressure therapy device.

In certain embodiments, a chamber element may be affixed to a flange element as an integral structure, as a unitary structure, or as discrete structures. The flange element provides mechanical support for the interface between the apparatus and the tissue of the user. As used herein a compliant conforming interface is defined as a flexible, shear absorbing and compressible surface capable of stretching, bending and or flexing to form an approximate air-tight seal between the chamber element and the user.

In certain embodiments, a compliant conforming interface between the therapy device and the individual varies in width and/or thickness around the circumferential dimension of the therapy device. By varying the conforming interface, the magnitude of forces applied to the tissue surface of the individual can be varied from point to point around the continuous contact area. In this manner, the force applied to the external surface of the individual at any point along the circumferential dimension of the sealing element may be made to be "constant." In this context, the term "constant" as used herein, refers to maintaining the force within about 20%, and more preferably about 10%, of the average force along the entire circumferential dimension of the sealing element, where the force at each point along the circumferential dimension of the sealing element is measured at the location on the width dimension of the flange element at which sealing element contacts the user.

Any and all vacuum, gas, or fluid pump types find use in the present invention, provided that a desired level of flow can be achieved by the selected pump. In certain embodiments, the pump may be connected to the apparatus via a hose or tube. For greatest mobility, a pump is preferably wearable by the patient and is battery powered, and most preferably the air pump is configured integrally to the appliance.

In certain embodiments, a vacuum pump may be a manual squeeze bulb, or may be electric and comprise a piezoelectric material configured to provide an oscillatory pumping motion. It is most preferred that the oscillatory pumping motion operates at a frequency greater than 500 Hz.

In those embodiments where the pump is configured integrally to the apparatus, a sealing feature between the pump and the appliance preferably forms an airtight seal. By way of example, a compliant sealing ring or lip seal may be provided within the opening into which the pump engages. The sealing feature may be provided integrally with the chamber element, and most preferably as a unitary structure with the chamber element. Alternatively, the compliant sealing ring and the chamber element are discrete structures In certain embodiments of a negative pressure device, the chamber element comprises one or more apertures creating vent elements that provide a controlled airflow into the chamber when the therapy device is mated to the individual and a therapeutic level of negative pressure is applied. The apertures, located distal to the intake of a pump element provide a flow of air through the chamber that may primarily assist to facilitate hysteretic control of a vacuum therapy range, and secondarily assist the exchange of air within the interior of the chamber. As used herein, hysteretic control is defined as the reaction of the control system within a range to change the flow rate of the vacuum pump to a perceived change in absolute barometric pressure within the chamber element of the negative pressure device. The range provides two points—an "on rise" point at which the pump is energized, and an "on fall" point at which the pump is turned off. The aperture(s) providing an airflow that is preferably between about 10 mL/min and about 300 mL/min, and most preferably between about 20 mL/min and about 150 mL/min, and still more preferably between about 40 mL/min and about 100 mL/min.

In some embodiments, the vent element can comprise an aperture and a filter element within the aperture, wherein the filter element comprises a pore size of about 1.0 µm or less, such as a pore size of about 0.7 am. The filter element can be configured as a replaceable element and the size adjusted to provide an airflow preferably between about 10 mL/min and about 300 mL/min, and most preferably between about 20 mL/min and about 150 mL/min, and still more preferably between about 40 mL/min and about 100 mL/min.

In yet another embodiment, the vent element can comprise one or a plurality of holes distal to the intake of the pump element and of a sufficiently small size to exclude debris from entering the chamber. The number of holes and diameter of the hole size further enables the desired airflow of preferably between about 10 mL/min and about 300 mL/min, and most preferably between about 20 mL/min and about 150 mL/min, and still more preferably between about 40 mL/min and about 100 mL/min, wherein the hole size is between about 25 um to about 200 um and more preferably an airflow of about 40 mL/min with a hole size between about 73 microns to about 83 microns Alternatively, the level of airflow can vary. In certain embodiments, the level of airflow tied to the therapeutic level of vacuum; that is, a higher level of vacuum can be accompanied by a higher level of airflow due to the differential in pressure between the atmospheric side of the vent elements and the interior of the chamber. In certain embodiments, the vacuum source may be used in a variable manner to maintain the therapeutic level of vacuum within a specified range rather than a single value, and the level of airflow can vary in concert with the level of vacuum.

In related aspects, the present invention relates to methods of applying negative, positive or neutral pressure therapy to an individual in need thereof, comprising mating a therapy device as described herein to the individual and applying a desired level of pressure within the chamber. In the case of a cNEP (continuous negative external pressure) airway support device, the therapy devices may increase patency of the airway of the individual. Such methods can be for treatment of sleep apnea; for treatment of snoring; for treatment of full or partial upper airway collapse, whether during sleep or during medical treatment where full or partial sedation is administered; for treatment of full or partial upper airway obstruction; for negative pressure treatment of a wound caused by, for example an injury or a surgery; etc.

DETAILED DESCRIPTION OF THE INVENTION

Figure 1:
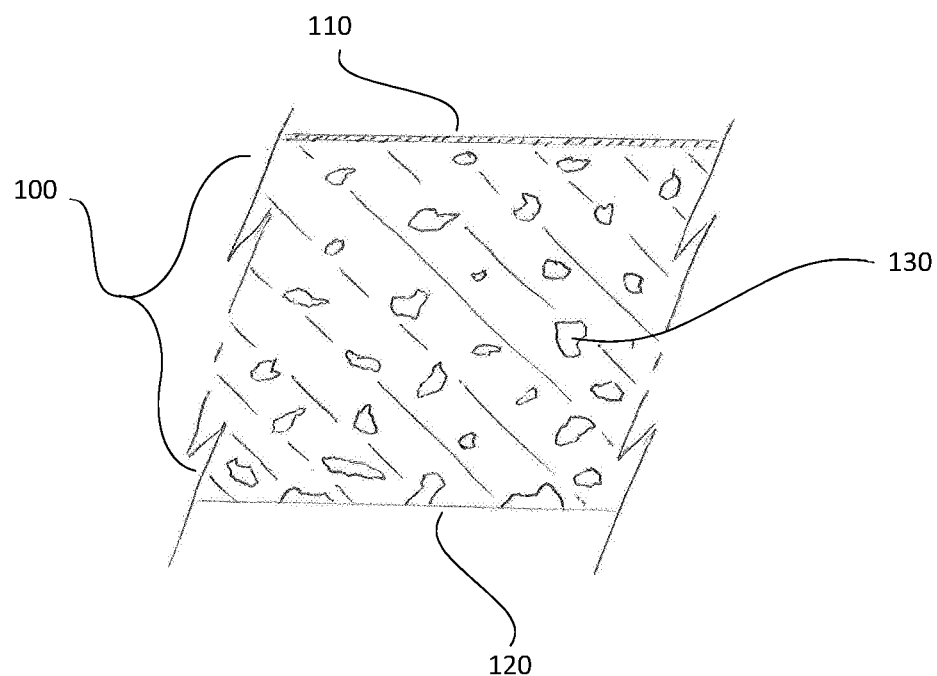
FIG. 1 is an illustrative drawing of a cross-section of an open cavity skinned foamed elastomer 100, comprising a viscoelastic foamed tissue interface surfaces 110, a non-contacting substrate interface surface 120 and one or more gas pockets within the foamed elastomer 130.

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

In the present invention, an appliance is configured to contact living tissue or similar surfaces comprising a viscoelastic foam. Ideally, the contact surface of the appliance provides an appropriate balance between viscoelastic properties that enable the material to adapt to anatomical differences between individuals as well as changes that may occur as a result of movement by a given individual—the former implying a low viscous modulus enabling the material to flow/adapt, the latter implying a low elastic modulus enabling the material to recover. Of particular note in various embodiments are a very low (tissue-like) durometer extending into the 000 scale range, an inherent tackiness, a closed-cell surface, enhanced cleanability, and enhanced durability.

In addition, the contact surface ideally comprises a level of tackiness to prevent an appliance from sliding on the living tissue that would otherwise result in skin abrasion or chafing, and to help maintain an air-tight seal between the appliance and the living tissue in both static and dynamic conditions. The contact surface should be tissue-like in stiffness, extremely low in skin sensitivity or allergic reaction, and be reasonably impervious to microbial growth. Finally, if used in a repeated-use application, cleaning must be facilitated such that, not only is the interface material not degraded, but dirt, grime, stubble, make-up, and/or perspiration is removable with surface tackiness maintained.

In achieving the object of the invention—i.e. a compliant interface between an appliance and living tissue—it has been determined that reducing the durometer of the elastomeric foam will result in a corresponding reduction in viscoelastic moduli (measured by storage and loss moduli). An increase in foaming agent concentration will have the result of reducing viscoelastic moduli albeit not as strong an influence as durometer.

It has also been determined herein that foaming of an elastomeric material may be used to achieve surface tackiness without the addition of tackifiers. A low concentration (e.g., less than 5% and preferably less than 3%) of foaming agent results in a compliant structure that, when loaded, has higher surface tackiness than its non-foamed variant.

Additionally, to enhance cleanability, the outer surface of the elastomeric foamed material may be "skinned-over" by means of how it is formed during fabrication, thereby closing the otherwise open-cell structure of the surface and replacing it with an integral closed, continuous surface that resists contamination.

The following are preferred viscoelastic properties of a viscoelastic foam for use in the present invention:

| | Preferably | More Preferably | Most Preferably |
|---|---|---|---|
| 1 Shore A Durometer w/1.5-3.0% Foaming Agent | | | |
| Elastic Modulus (kPa) | 0.3-27.8 | 0.8-23.5 | 1.2-19.2 |
| Viscous Modulus (kPa) | 0.5-5.4 | 0.6-4.6 | 0.7-3.9 |
| 5 Shore A Durometer w/1.5-3.0% Foaming Agent | | | |
| Elastic Modulus (kPa) | 0.3-19.0 | 0.9-16.8 | 1.4-14.6 |
| Viscous Modulus (kPa) | 0.4-3.6 | 0.5-3.3 | 0.6-2.9 |
| 1 Shore A Durometer + 1.5% Foaming Agent | | | |
| Elastic Modulus (kPa) | 1.4-27.8 | 1.7-23.5 | 2.0-19.2 |
| Viscous Modulus (kPa) | 0.8-5.4 | 0.9-4.6 | 1.0-3.9 |
| 1 Shore A Durometer + 3.0% Foaming Agent | | | |
| Elastic Modulus (kPa) | 0.3-8.1 | 0.8-7.6 | 1.2-7.0 |
| Viscous Modulus (kPa) | 0.5-2.4 | 0.6-2.2 | 0.7-2.0 |
| 5 Shore A Durometer + 1.5% Foaming Agent | | | |
| Elastic Modulus (kPa) | 0.3-19.0 | 0.9-16.8 | 1.5-14.6 |
| Viscous Modulus (kPa) | 0.6-3.6 | 0.7-3.3 | 0.8-2.9 |

-continued

|  | Preferably | More Preferably | Most Preferably |
|---|---|---|---|
| 5 Shore A Durometer + 3.0% Foaming Agent | | | |
| Elastic Modulus (kPa) | 0.7-14.2 | 1.0-12.5 | 1.4-10.7 |
| Viscous Modulus (kPa) | 0.4-3.5 | 0.5-3.1 | 0.6-2.6 |

In certain embodiments, the viscoelastic foam defines one or more surfaces of a negative, positive or neutral pressure therapy device that contacts living tissue or similar surfaces and is designed to maximize comfort and seal efficiency, ultimately optimizing device efficacy and user compliance. In certain embodiments. a non-tissue contacting portion (non-contacting portion) of the appliance provides support for the viscoelastic foam element and an interface between the appliance and the viscoelastic foam that contacts the living tissue. In certain embodiments, the viscoelastic foam may be applied to a negative pressure chamber configured to cover a portion of the body as described below for use in opening the upper airway of an individual when placed upon the anterior neck region of a subject over a surface corresponding to approximately the upper airway of the subject.

Figure 5:
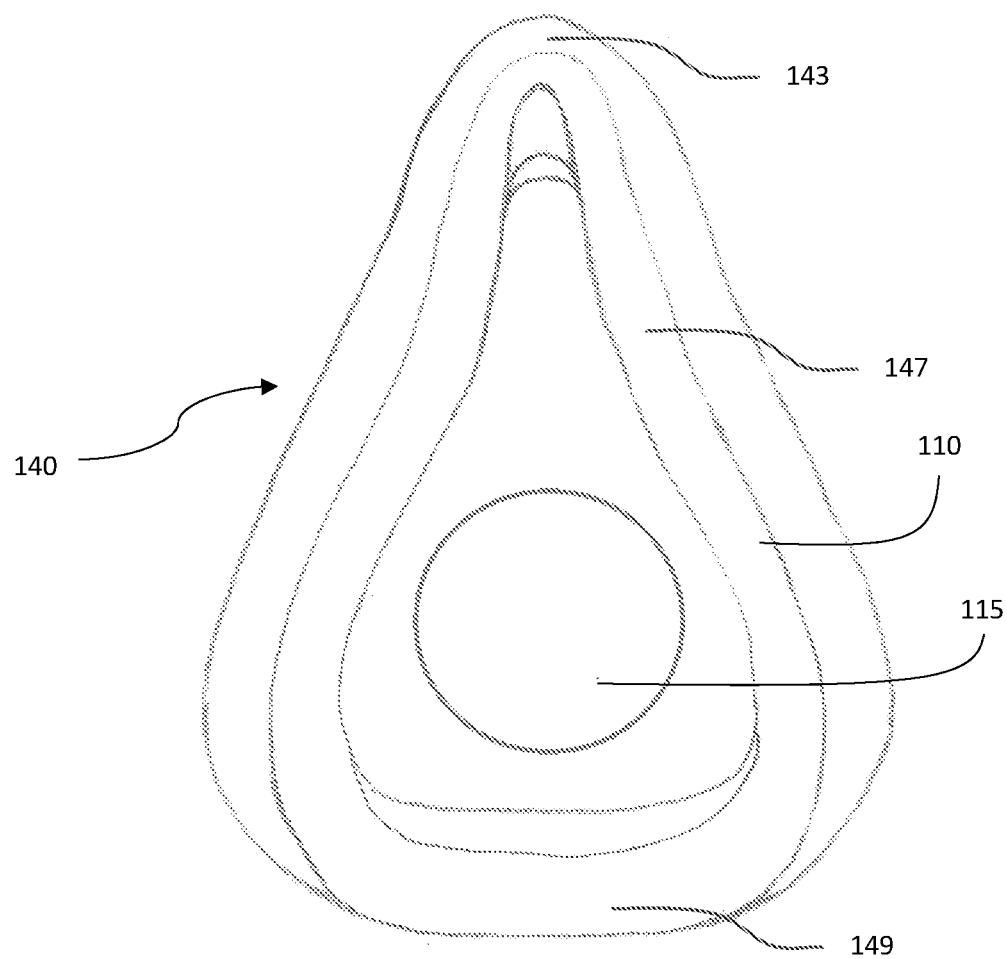
FIG. 5 is an illustrative drawing of the rear surfaces of a partial face mask 140, comprising a viscoelastic foamed tissue interface 110, an aperture for an air pump 115, the approximate location of the nose bridge 143, the approximate location of the cheek bone 147 and approximate location of the chin bone 149.
Figure 6:
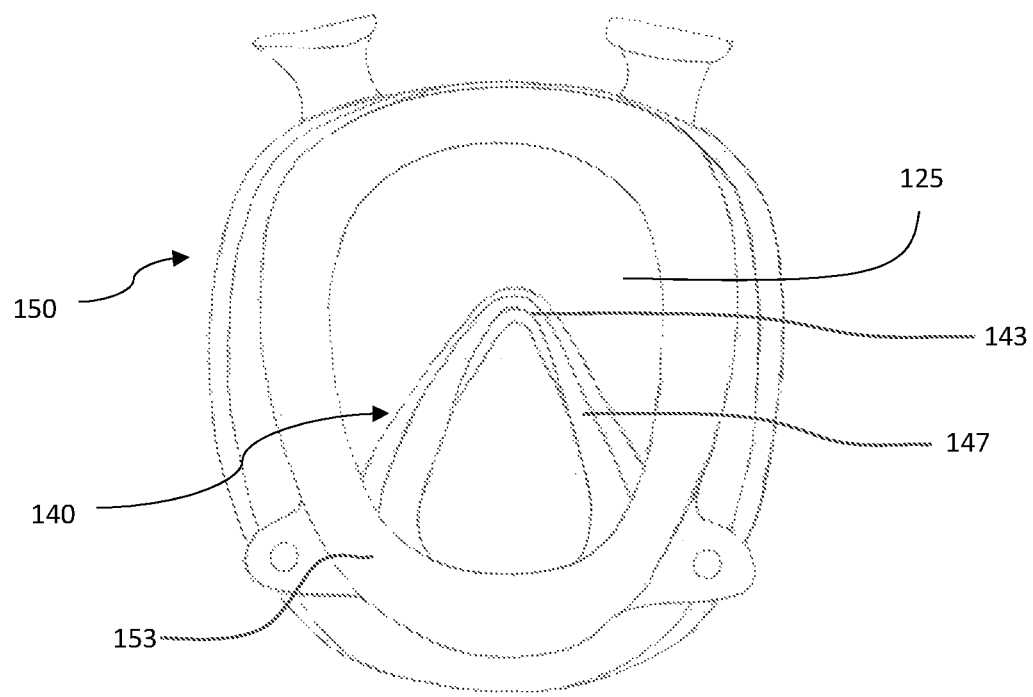
FIG. 6 is an illustrative drawing of the rear surfaces of a full face mask 150 comprising an outer perimeter face sealing surface 153, a face shield 125, a partial face mask 140 interior to the outer perimeter face sealing surface 153, the approximate location of a nose bridge 143, the approximate lection of the cheek bone contacting surface 147, (the approximate location of the chin bone contacting surface 149 being obscured by the lower portion of the outer perimeter face sealing surface 153).

This exemplary application of the technology is not meant to be limiting. The viscoelastic foam may further find use as one or more contact surfaces of additional appliances meant for limited or prolonged contact with or treatment of tissue sites, including but not limited to medical appliances for example, infusion sites or sites of living tissue contact for biometric data gathering for example, ECG and EKG electrodes, continuous glucose monitoring (CGM) systems, tracheal tubes, catheters, medical balloons, partial face masks (FIG. 5) wherein FIG. 5 shows the rear surfaces of a partial face mask 140, comprising a foamed elastomeric tissue interface 110, an aperture for an air pump 115, the approximate location of the nose bridge 143, the approximate location of the cheek bone 147 and approximate location of the chin bone 149, full face masks (FIG. 6), wherein FIG. 6 shows the rear surfaces of a full face mask 150 comprising an outer perimeter face sealing surface 153, a face shield 125, a partial face mask 140 interior to the outer perimeter face sealing surface 153, the approximate location of a nose bridge 143, the approximate location of the cheek bone contacting surface 147, (the approximate location of the chin bone contacting surface 149 being obscured by the lower portion of the outer perimeter face sealing surface 153). Wherein the outer perimeter face sealing surface 153 and partial face mask 140 sealing surface can be, fully or partially covered with the foamed elastomeric material 110.

The viscoelastic foam may further find use as one or more contact surfaces of additional appliances meant for limited or prolonged contact with or treatment of tissue sites, including but not limited to eye protection masks, colostomy bags, ear plugs, ear phones, head phones, goggles, sporting equipment and so on. The viscoelastic foam provides for compliance in all directions including compression and sheer properties that closely mimic the living tissue it contacts for a tissue friendly interface. Further, the viscoelastic foam element is durable, abrasion resistant, shear absorbing, compressible, conformable, comfortable and washable. The viscoelastic foam may also find use as the tissue interface of a scuba or like mask wherein the viscoelastic foam is fluidly sealed to liquid such that at a pressure of about 1 atm for at least 10 minutes no more than 10% of the mask fills with liquid, where the liquid may be fresh water, sea water, oil or any substance that flows freely but is of a constant volume.

In certain embodiments, the viscoelastic foam element comprises density, durometer and probe tack properties as follows:

| Viscoelastic foam Material Fabrication Process | Range Preference | Density (g/cm$^3$) | Durometer (Shore) | Tack (mJ/cm$^2$) |
|---|---|---|---|---|
| Open Cavity | Preferably | 0.1-0.8 | <10 (00) | 0.1-9 |
| | More Preferably | 0.2-0.7 | <50 (000) | 0.3-7 |
| | Most Preferably | 0.3-0.5 | 5-30 (000) | 0.5-5 |
| Closed Cavity | Preferably | 0.3-0.9 | <10 (00) | 0.1-9 |
| | More Preferably | 0.5-0.8 | <80 (000) | 0.3-7 |
| | Most Preferably | 0.6-0.7 | 20-40 (000) | 0.5-5 |

Wherein the (EFMFP) is the elastomeric foam Material Fabrication Process and is defined by the manner in which the viscoelastic foam is cured. EFMFP is categorized by either an "Open Cavity" process or a "Closed Cavity" process. As used herein, an open cavity viscoelastic foam material fabrication process is defined by the application of a viscoelastic foam element upon a substrate for curing outside a molding feature. In open cavity processes, the viscoelastic foam may simply be applied to the substrate and allowed to cure in any desired manner for example at room temperature, under the application of heat, UV or a combination thereof for example. As used herein, a closed cavity viscoelastic foam material fabrication process is defined by the application or injection of a viscoelastic foam element into an enclosed mold containing a substrate and generally under vacuum for curing the viscoelastic foam element to the substrate within the mold, for example the process of overmolding. Cure in these processes can similarly be achieved in any appropriate fashion, for example through the addition of catalysts, heat, UV or a combination thereof.

Wherein density is defined as the degree of consistency measured by the quantity of mass of a substance per unit volume, for example, grams per cubic centimeter (g/cm$^3$). In open cavity viscoelastic foam material fabrication processes, the density of the viscoelastic foamed material is preferably between 0.1-0.8 g/cm$^3$, more preferably between 0.2-0.7 g/cm$^3$ and most preferably between 0.3-0.5 g/cm$^3$. In closed cavity viscoelastic foamed material fabrication processes, the density of the viscoelastic foamed material is preferably between 0.4-0.9 g/cm$^3$, more preferably between 0.5-0.8 g/cm$^3$ and most preferably between 0.6-0.7 g/cm$^3$.

Wherein durometer is defined as a measure of hardness measured by the ASTM D2240 scales. In open cavity viscoelastic foam material fabrication process, the durometer is preferably less than about 10 Shore 00, more preferably less than about 50 Shore 000, and more preferably between about 5 and 30 Shore 000. In closed cavity viscoelastic foam material fabrication processes, the durometer is preferably less than about 10 Shore 00, more preferably less than about 80 Shore 000 and most preferably between about 20-40 Shore 000.

Wherein the Probe Tack is defined as the force required to separate an adhesive-like element and the adhered probe as measured by the ASTM D2979 Standard Test Method for Pressure-Sensitive Tack of Adhesives. In open cavity viscoelastic foam material fabrication process, the Probe Tack is preferably less than about 9 mJ/cm$^2$, more preferably less than 7 mJ/cm$^2$, and more preferably between about 5 mJ/cm$^2$. In close cavity viscoelastic foam material fabrication processes, the Probe Tack is preferably less than 9 mJ/cm$^2$, more preferably less than about 7 mJ/cm$^2$ and most preferably between about 5 mJ/cm$^2$.

In certain embodiments, the viscoelastic foamed material element is a foamed silicone rubber material that is produced by blending a combination of silicone rubber and a foaming agent, resulting in a foam cellular structure that increases in thickness upon curing preferably between 50 to 300%, and more preferably 75 to 250%, and most preferably 100 to 200%.

In certain embodiments, the compliant conforming interface comprises a viscoelastic foamed material layer that is preferably in the thickness range of 0.030" to 0.375", or more preferably 0.050" to 0.250", or most preferably 0.075" to 0.150".

Foaming agents are used for producing silicone foams in room temperature or heat-curable silicone elastomer systems. Foamed silicone rubber materials are designed to be conformable. Catalyst addition (e.g iron catalyst, a cobalt catalyst, a zinc catalyst, a titanate catalyst, a tin catalyst, a platinum catalyst, or an acid catalyst) rapidly yields a silicone rubber foam at room temperature. A foam cellular structure may be created by the release of gases during the curing process. Foams can also be created through the use of certain additives such as ammonium bicarbonate. Such an additive can create a cellular foam from a high consistency rubber (HCR) or a liquid silicone rubber (LSR) via the application of heat.

A high consistency rubber consists of a high molecular weight silicone polymer, optionally combined with a filler such as silica, to produce a material that can be molded, extruded, or calendared into a useful end-product. Liquid silicone rubbers (LSR), like HCRs, may be reinforced with silica, but typically use lower molecular weight polymers. LSRs are often pumped with an injection-molding machine and cured to form a molded part.

In certain embodiments, the viscoelastic foam may further comprise a reinforcing filler wherein the addition of a reinforcing filler can significantly improve the elastomeric mechanical properties of the viscoelastic foam such as stiffness, tensile strength, tear-strength and flex fatigue for example. Reinforcing fillers may be selected from a group containing for example an acidic filler such as fumed silica, silica, silica aerogel, silica xerogel, titanium dioxide, diatomaceous earth, iron oxide, aluminum oxide, zinc oxide, quartz, calcium, carbonate, magnesium oxide, carbon black, graphite, glass fibers, glass micro spheres, glass micro balloons, glass beads, carbon fibers, silicon carbide, polystyrene beads, and metal fibers.

In certain embodiments, the tissue interface portion comprises a silicone rubber material that is preferably an HCR and more preferably an LSR material, in combination or in part. The durometer of the silicone rubber is preferably in the range of approximately Shore A durometer of 1 to 20, and more preferably approximately Shore A durometer of 1 to 10. The silicone rubbers may further be foamed creating a three-dimensional network of hydrophobic polymer chains that can be crosslinked either physically or chemically. Due to the foamed LSR material's significant gas content, foamed LSRs can closely resemble natural soft tissue. Foamed properties can be achieved through the addition of a foaming agent added to the silicon rubber material, for example an ammonium bicarbonate dispersed in a vinyldimethyl-terminated polydimethylsiloxane polymer. In these examples, the ratio of foaming agent to silicone rubber by weight is preferably in the range of approximately 0.1% to 10%, and more preferably approximately 0.5% to 5%, and most preferably approximately 1.5% to 3%. Additional agents employed in the formation of foamed LSR may include, but are not limited to, platinum catalysts and organic tin compound catalysts.

In certain embodiments, the compliant conforming interface element comprises a viscoelastic foamed material with a tissue interface that has a surface tension sufficiently high so as to mitigate or eliminate sliding between the patient tissue and the compliant conforming interface element. Tackiness of the tissue interface further contributes to accommodating a broader cross-section of anatomical variation and creating the necessary interface seal.

Further desired attributes or aspects of the device can be defined through additional material characteristics including but not limited to, specific gravity, tensile strength, elongation, tensile modulus, tear strength, durometer, and Probe Tack, for example.

Wherein specific gravity is defined as the ratio of the density of a substance to the density of a reference substance, for example the ratio of an elastomeric material to the density of water. In embodiments of the device, the specific gravity of the viscoelastic foamed material is between about 0.49 g/cm to about 0.72 g/cm.

Tensile properties (as measured using ASTM D412, for example) can obtain values for tensile strength, elongation and tensile modulus for example.

Wherein tensile strength is defined as the capacity of a material to withstand elongation loads, whereby a tensile strength (ultimate tensile strength) is measure by the maximum stress that a material will withstand while being stretched before fracture. In embodiments of the invention the tensile strength of the viscoelastic foamed material is preferably between about 31 psi to about 114 psi and more preferably between about 31 psi and about 62 psi.

Wherein elongation is defined as the increase in the length of the viscoelastic foamed material measured after fracture and expressed as a percentage of the original gauge length. Wherein gauge length is defined as the distance along the specimen upon which elongation calculations are made. In embodiments of the invention the elongation of the viscoelastic foamed material is between about 438% and about 817% and more preferably between about 438% and about 747%.

Wherein tensile modulus is defined as a measure of stiffness defining the relationship between stress and strain. In embodiments of the invention the tensile modulus of the viscoelastic foamed material is between about 5 MPa and about 10 MPa and preferably between about 6 MPa and about 7 MPa.

Wherein tear strength (as measured using ASTM D624, for example) measures the force per unit thickness (pounds per inch Ppi) required to rupture or start a tear through a sample. In aspects of the invention, the viscoelastic foamed material has a tear strength between about 8 Ppi and about 32 Ppi and more preferably between about 9 Ppi and about 14 Ppi.

In aspects of the invention further attributes of the viscoelastic foamed material may include tack properties that are maintained over time for example, times beyond curing that include storage, usage and or washing. In certain embodiments the probe tack values of the viscoelastic foamed material as measured by the ASTM D2979 Standard Test Method for Pressure Sensitive Tack of Adhesives using a Polyken Probe tack PT-1000 instruments is maintained between about 0.43 mJ/cm² and about 2.52 mJ/cm² for up to a week or more of curing with a maintenance of probe tack of about 65% or more at a time period of about 4 weeks or longer, preferably a maintenance of probe tack of about 73% or more for a period of about 4 weeks or longer and most preferably a maintenance of probe tack of about 83% or more.

In certain embodiments, an antimicrobial composition is added to the viscoelastic foam element. Antibacterial, antifungal, and antiviral properties may be conveyed in any appropriate matter for example the addition of silver salts in the form of silver sulfates, silver citrates, silver acetates, silver carbonates, silver lactates and silver phosphates, for example. Additionally, zeolites containing approximately 15% by weight of silver ion may also be used. Other suitable materials (e.g., polyhexamethylenebiguanide) are known in the art.

In certain embodiments, the compliant conforming interface element comprises a viscoelastic foamed material that is preferably affixed mechanically, or more preferably bonded by means of an interposing adhesive layer, or most preferably dispensed and cure-bonded directly without any mechanical means or additional adhesives—onto a tissue interface portion of an appliance to form a leak-free tissue interface. In certain embodiments, Overmolding may be employed to provide mechanical features on the appliance for attachment and retention of the foam.

In certain embodiments, the compliant conforming interface element comprises a viscoelastic foamed material that is sheet-formed, cured, and subsequently form-cut and either affixed mechanically, or adhesive bonded onto the tissue interface portion of an appliance using an interposing adhesive layer—RTV (room temperature vulcanizing) silicone rubber for example—to form a leak-free tissue interface.

In certain embodiments, the compliant conforming interface element comprises a multilayer construction of foamed silicone rubber material that is sheet-formed and cured onto a milled or calendared HCR material which latter material serves as an adhesion layer that is heat-bonded onto the tissue interface portion of an appliance to form a leak-free interface.

Figure 2:
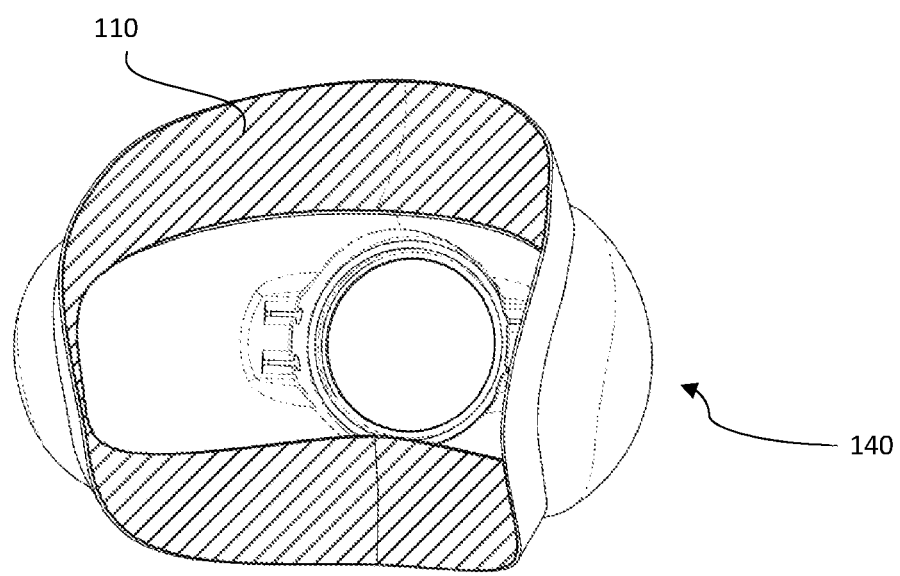
FIG. 2 is an illustrative drawing of a cNEP airway support device 140 showing a cross-hatched area representing the tissue interface surface fully covered with a foamed elastomer 100.
Figure 3:
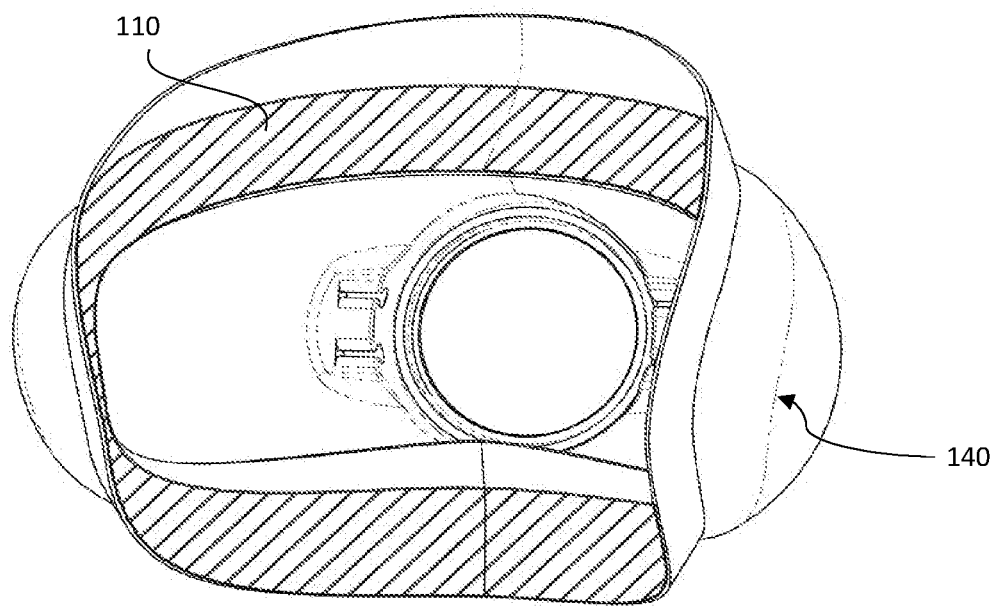
FIG. 3 is an illustrative drawing of a cNEP airway support device 140 showing a cross-hatched area representing the tissue interface surface partially covered with a foamed elastomer 100 such that the foamed elastomer forms a predominant portion of the skin contacting area of the device.

In certain embodiments, the compliant conforming interface element comprises a viscoelastic foamed material that may be over-molded directly onto the flange element of the collar and cured to form a leak-free tissue interface (FIG. 2, 110). As used herein, over-molding is the process of adding material to an already molded shape creating a final product that is partially or fully covered by the subsequent material and is slightly larger than the original part.

In certain embodiments, the present invention comprises a viscoelastic foamed material that is continuously dispensed across the width of the non-contact surface 120 of an appliance wherein the width of the foamed silicone rubber is either constant or varying across the surface of the substrate of the appliance and cured to form a leak-free tissue interface. As seen in FIG. 2 showing an illustrative drawing of a cNEP airway support device 140 wherein the a crosshatched area represents the tissue interface surface partially covered with a foamed elastomer 100

Figure 4:
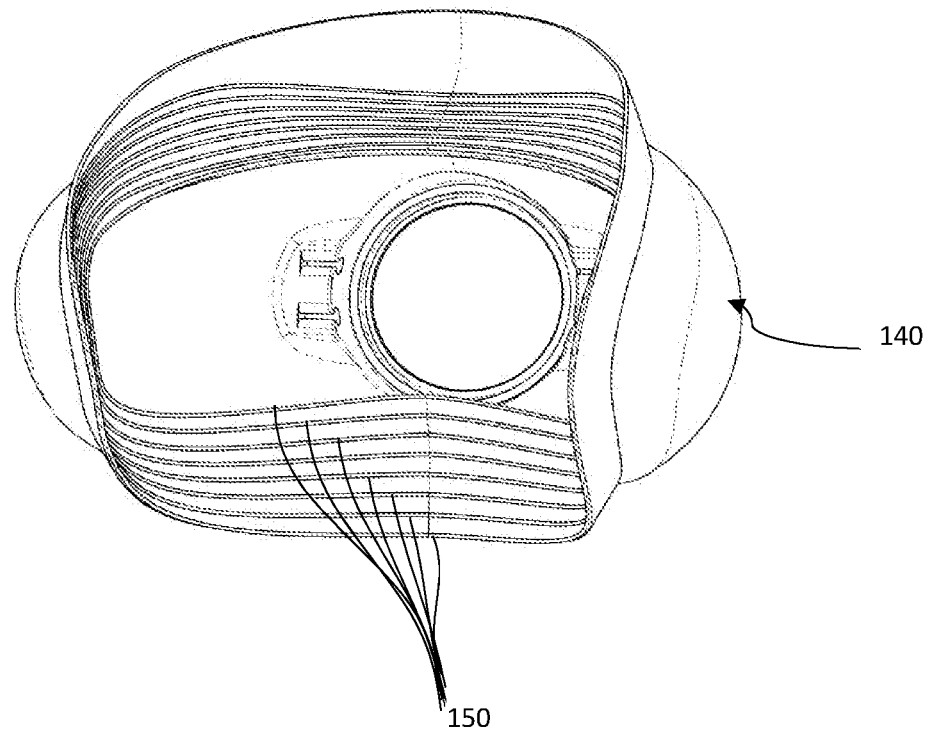
FIG. 4 is an illustrative drawing of a cNEP airway support device 140 with uninterrupted concentric beads 150 of foamed elastomer contiguously positioned at a fixed pitch across the width of the viscoelastic foamed tissue interface surface 110

In certain embodiments, a viscoelastic foamed material is continuously dispensed and cured in one or more discrete concentric annular rings and/or ribbons corresponding with the shape of the tissue interface portion of an appliance (FIG. 4, 150). Wherein an annular ring is defined as a pattern bounded by and containing the area between two concentric circles or shapes. These discrete concentric annular rings or ribbons may be of the same or varying thickness and or same or varying width or a combination thereof on the non-contacting portion of the appliance. Said rings or ribbons may preferably be dispensed to include pitch spacing between them so as to be independent and free-standing upon heat curing, or more preferably dispensed with sufficiently narrow pitch spacing between them such that the rings and/or ribbons expand and knit together upon heat curing to form a leak-free tissue interface. As used herein, knit together is defined as the contact or flowing together of the outer edges of one or more of the rings or ribbons forming a uniform feature and or a feature of peaks and valleys of the rings or ribbons. Wherein the peaks are defined as thicker regions of the rings or ribbons as compared to the valleys which are defined as thinner regions of the rings of ribbons. As used herein, pitch separation is defined as the dimensional distance between two recurring features for example the dimensional separation between the centerlines of concentric annular rings of viscoelastic foamed material.

In certain embodiments, the tissue interface portion comprises a viscoelastic foamed material that is continuously dispensed and cured in a continuous spiral ring and/or ribbon corresponding with the shape of the tissue interface portion of the appliance. Said continuous spiral ring or ribbon may preferably be dispensed to include pitch spacing between the successive dispensed rings/ribbons so as to be independent and free-standing upon heat curing, or more preferably dispensed with sufficiently narrow pitch spacing between them such that the successive rings and/or ribbons expand and knit together upon heat curing to form a leak-free tissue interface.

In certain embodiments, the tissue interface portion comprises a viscoelastic foamed material that is dispensed in a dot matrix pattern for example with sufficiently narrow pitch spacing between the dispensed elements such that they expand and knit together upon heat curing to form a continuous leak-free tissue interface.

In certain embodiments, the foamed silicone rubber of the present invention will be sufficiently supple and conformable to facilitate some pre-existing or overnight growth of stubble without compromising the necessary therapeutic interface seal. In a viscoelastic foamed material, the range of suitable silicone rubber durometer and foaming agent concentration is preferably in the range of 1 to 10 Shore A and 1.5 to 3% respectively. The resultant viscoelastic foam having a final durometer of less than 10 Shore 00 and more preferably a final durometer range of approximately 1 to 40 Shore 000.

In certain embodiments, the compliant conforming interface element comprises a foamed silicone rubber material whose foam cellular structure is preferably produced by a subtractive process wherein salt of a given particle size and concentration is uniformly blended with an LSR formulation and subsequently washed-out (i.e. dissolved or subtracted) leaving behind a cellular structure, and more preferably produced by a gas expansion process wherein a foaming agent of a given particle size and concentration is uniformly blended with an LSR formulation and subsequently expanded by the application of heat to result in a cellular structure.

Optionally, an adhesive layer or gel is located on the surface of the compliant conforming interface element that makes contact with the user. Silicone gels for example are designed to be soft and conformable. They achieve their gel-like consistency by having less crosslinking than is typical of elastomers and are generally not silica-reinforced. Uncured gels are easily pourable and can be mixed by hand and molded into finished parts. An adhesive or gel layer aims to reduce movement of the device on the wearer as well as enhance the seal and cushioning on the wearer. These elements are configured to maintain an approximate uniform contact pressure with minimized pressure variations along the tissue of an individual through all points of contact of the therapy device on a patient. By "minimized pressure variation" means a pressure at any point between the contact surface of the sealing element and the patient's tissue varies by no more than about 20%, and preferably no more than about 10% or about 5%, from the average pressure across the entire contact surface. The outer contact surface, as used herein, is the surface of the sealing element of the therapy device that makes contact with the tissue of the individual forming the contact and sealing tissue interface portion of the appliance.

In certain embodiments, a therapy device comprised of a chamber and a sealing element is configured to be the contacting surface between the chamber and the user described herein is configured to provide for regional load equalization over the interface between a negative pressure therapy device and the three-dimensional varying tissue surface of the user so as to maintain a near uniform contact pressure over this non-uniform surface.

In particular, the therapy device referred to herein relates but is not limited to an external therapy appliance for relieving upper airway obstruction. U.S. patent application Ser. Nos. 12/002,515, 12/993,311 and 13/881,836 which are hereby incorporated by reference in their entirety including all tables, figures and claims, describes a therapy appliance for relieving airway obstruction. Increasing the patency of the upper airway of an individual alleviates conditions such a snoring, sleep apnea, full or partial upper airway collapse whether during sleep or during medical procedures where sedation has been administered. As described therein, a device is configured to fit under the chin of a user at an external location corresponding to the soft tissues overlying the upper respiratory passages of the neck.

In various embodiments, the viscoelastic foamed material characteristics may include an ability to maintain desired material characteristics at a range of varied temperatures. These characteristics further enable the ability of the tissue contacting surface of the viscoelastic foamed material of a device to conform to a moving and flexing living tissue interface surface, tissue-like interfacing surfaces as well as a non-tissue contacting surface that may or may not be a moving or flexing surface, for example surfaces of a rigid or flexible wearable appliance or features thereof.

As described herein the viscoelastic foamed material may find use as an interface between living tissue surfaces, tissue-like surfaces and or non-tissue surfaces of a rigid or flexible wearable appliance or features thereof. The viscoelastic foamed material providing a compliant, comfortable fitting interface enabling and encouraging usage for periodic or prolonged usage of devices. Although the duration of use may depend on application, duration of therapy needed and protection etc., the viscoelastic foamed material can alleviate negative limitations of fit and feel of appliances not including the viscoelastic foamed material.

Figure 7:
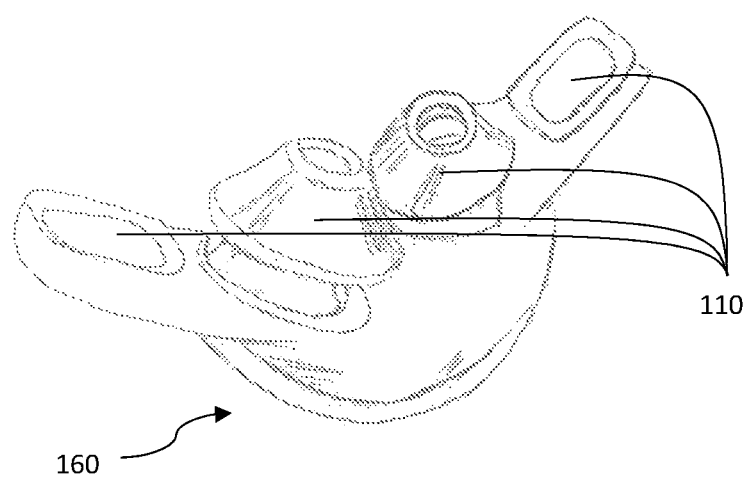
FIG. 7 is a rear view of a nasal cushion 160 comprising at the nasal cups and outer tissue contact surfaces, viscoelastic foamed tissue interface surfaces 110.

Appliances benefiting from the viscoelastic foamed material interface may be prescribed, and/or required by a Chemical Hygiene Plan (CHP) for example. and may include but are not limited to interfaces between medical and or therapy devices and a user (prosthetic devices, positive or negative pressure therapy devices, CPAP appliances, cNEP appliances, laryngeal mask airway (LMA's), nasal prongs, nasal pillows (FIG. 7), airway insertion devices, catheter protection/sealing systems and so on). Further applications may include but are not limited to interfaces between civilian or military Personal Protective Equipment (PPE) and a user. Applications can further include respiratory protection, particle and or gas mask interface surfaces and/or interface surfaces of protective clothing or protective barriers used to seal regions of an appliance and tissue, tissue-like and or non-tissue surfaces. Applications can be found in Level A, Level B, Level C and/or Level D, OSHA-rated protection including but not limited to, pressure demand, self-contained breathing apparatus (SCBA), gloves, foot and eye protection, earplugs, ear muffs (for noise dampening and protection), knee, elbow and/or wrist pads, helmets, hats, full or partial-faced positive or negative pressure respirators and or full body suits, theatrical appliances including masks, wigs, ears, noses, forehead prosthetics, cheeks, chins, brow appliances and small makeup FX pieces and so on.

In various embodiments the foamed elastic material may be in the form of an injectable or pre-formed material to fill winkles, furrows, acne scars or to add volume to lips and cheeks, for example. Silicone rubber is less expensive than fillers like collagen and Restylane, easy to work with and side effects occur in less than 1% of patients. Further, fillers such as collagen and Restylane are absorbed by the body within about 6 months making silicone a more permanent option. Uncontrolled or free silicone is generally not well tolerated in the body making a cured coating, curing injection or pre-cured implant preferable. As used herein, a cured coating is defined as a layer of the viscoelastic foamed material that is applied to a desired surface in an un-cured state (possibly liquid or gel) and cured to its final viscoelastic foamed form via heat, UV or a chemical catalyst for example. As used herein a curing injection is defined as the injection of the uncured viscoelastic foamed material and a catalyst into a desired location wherein the viscoelastic foamed material can cure to its final viscoelastic foamed form where placed through injection. As used herein a pre-cured implant is defined as a viscoelastic foamed material that is cured to a desired shape and utilized or implanted at a desired location.

In certain embodiments the viscoelastic foamed material may find use as a coating for catheters, guidewires, stents, grafts and or stent-grafts by protecting vessel walls during insertion, lowering deployment or extraction forces of the devices as well as providing a tissue-like interface between all, part or selected portions of the devices. Further, the viscoelastic foamed material can be mixed with anti-proliferative agents to reduce the restenosis to improve clinical outcomes. As used herein, deployment force is defined as the outward force exerted by a device such as a stent as it deploys from its initial diameter to its working diameter, as measured within a glass tube having the correct internal diameter. Suitable testing machines (WL2100; Withlab, Gunpo, Gyeonggi-do, Korea) for measuring deployment force are known in the art.

In further embodiments the viscoelastic foamed material may find use as a ureteral stent or a coating for ureteral stents by protecting the ureteral wall, kidney, bladder and urethra providing a tissue-like structure and or interface between all, part or selected portions of the stent.

In certain embodiments, the viscoelastic foamed material may find use in repair of non-ruptured aortoiliac aneurysm (AAA) or conditions of the like wherein, for example, a stent graft, comprising a stent portion for anchoring to the aortic wall and a graft portion, comprising a network of channels is used to repair an aneurysm. The stent graft is delivered within a catheter in a compressed state and when released from the compressed state the stent engages the vessel wall and the graft is expanded to direct blood flow. The aneurysm is then sealed via filling the space between the graft and vessel wall by injecting the filing material either directly or by inflating sealing chambers, endo-bags and other support-type structures (ring-shaped ribs for example) using appropriate filling material, for example the viscoelastic foamed material. The components of the viscoelastic foamed material is mixed to begin the cross-linking to form the fill of viscoelastic foamed material. Mixing of the components may occur prior to filling the graft or mixed within the graft during fill. The viscosity remains low after mixing to aid in fill, thickens changing from liquid to form a soft, compliant, yet firm solid. The mixed viscoelastic foamed material may further comprise a contrasting material to aid the physician to visualize appropriate deployment wherein the material is injected into the inflatable sealing chambers of a graft.

In certain embodiments the viscoelastic foamed material may be used as an interface between living tissue and a prosthetic device. The viscoelastic foamed material may satisfy critical features necessary for supporting the structure of living tissue, living tissue maintenance, living tissue repair as well as provide a more favorable functional relationship between a prosthetic device and the living tissue. The viscoelastic foamed material can be designed to reproduce the structural hierarchy of complex tissues by varying physical properties of the viscoelastic foamed material to more favorably interface between all or part of the living tissue and a prosthetic. The viscoelastic foamed material may be used to form a layer between the living tissue and a prosthetic in a uniform or varying thickness and in a uniform or varying durometer to accommodate variations in the living tissue and the prosthetic. Further, the probe tack of the viscoelastic foamed material may favorably bias adhesion of the viscoelastic foamed material to the living tissue and favorably bias adhesion of the viscoelastic foamed material to the prosthetic providing a more favorable interface between the prosthetic and the user. Further, air pockets inherent to the viscoelastic foamed material may further provide favorable adhesion between the prosthetic and the user during instance of water saturation either by perspiration or other instance of water contact by capturing and or removing moisture between the living tissue and the viscoelastic foamed material while substantially maintaining the probe tack of the viscoelastic foamed material.

For purposes of the patent application, the term "about" refers to +/−10% of any given value.

The negative pressure therapy device of the present invention comprises a flexible membrane element, an aperture through the flexible membrane element and a compliant tissue interface portion positioned along the edge or face of the flexible membrane element along the circumferential dimension of the tissue interface portion to form an airtight junction between the tissue interface portion and the flexible membrane element. The junction between the non-contacting portion of the tissue interface portion and the chamber element is referred to herein as the "root" of the junction. As used herein a compliant element is defined as a one that is flexible, for example the compliant tissue interface portion, though in the approximate shape of the contact surface a target therapy area is flexible as to accommodate variation.

As used herein, the term "circumferential dimension" refers to a continuous location along the width of the tissue interface portion and in some cases, for example where the chamber element makes continuous contact with the non-contacting portion of the appliance. As used herein, the "root" is the location at which the chamber element contacts the non-contacting portion of the appliance and is of a width enclosed by the thickness of the chamber element. The chamber element may be affixed to the non-contacting portion of the tissue interfacing element as an integral structure, unitary structure or discrete structures. An "integral structure" refers to a structure that is a complete piece formed by joining two or more components which, once joined, become a single piece that is not separable without destroying the device. A "unitary structure" refers to a structure that is a singular structure formed or molded as a single piece. Two elements are "discrete structures" if the two (or more) structures form a single working structure, but retain individual characteristics and can be separated in the normal course of use of the single working structure and then reassembled.

Surface variation of the therapy site, both permanent and occasional (i.e., the shape of the mandible, transition points from neck to mandible, tissue types, scars, facial hair and/or tissue blemishes differential forces applied to different portions of the seal caused by movement of the wearer, etc.) can undesirably disrupt the seal between the negative pressure therapy device and user. The present invention provides devices, systems and methods of use that can accommodate varying facial contours/features and adapt to movement, resulting in greater comfort, reduced vacuum leakage and improved therapeutic efficacy.

The flexible membrane element and the sealing element of the appliance incorporate cantilever-like structures, hoop load-like structures and or a combination of the two, adapted to have sectional properties that allow for stiffness, flexibility and uniform regional compliance and/or force load on the tissue surface of the individual. As used herein, "regional compliance" refers to a property of the device that permits the device to "mold" itself to a surface and or surface variation on the contact surface with the wearer. As described hereinafter, uniform regional compliance is provided, in part, by the sectional properties or structural features associated with a region on the chamber element, sealing element or both.

The sealing element may be in the form of a flange comprising a flexible, elastic material that can be uniform in thickness and width but also vary in thickness and width to achieve the structural properties desired at locations along the contact surface of the therapy device. Further, the location of the chamber element at the root location of the flange of the sealing element may be varied to adjust and equalize the contact pressure of the therapy device when a therapeutic level of negative pressure is applied. U.S. Provisional Patent Application No. 62/281,063 filed: Jan. 20, 2016, titled: "Device and Method for Opening an Airway," and incorporated herein by reference, discusses variation of flange and chamber characteristics for the balancing of contact pressure In certain embodiments the sealing element may be a compliant tissue interface element containing one or a series of layers, including a foamed silicone rubber layer to provide for a cushioning surface. The inner surface of the flange being that which makes contact with the flexible membrane element and the outer surface of the compliant tissue interface element being that which makes contact with the tissue of the user. U.S. Provisional Patent Application No. 62/260,211 filed, Nov. 25, 2015 titled: "Chamber Cushion, Seal and Use Thereof", incorporated herein by reference discusses such a cushioned sealing element.

The tissue interface portion of the appliance is adapted to have sectional properties that allow for flexibility and uniform regional compliance. As used herein, "uniform regional compliance" refers to a property of the compliant tissue interface element that permits the compliant tissue interface element to "mold" itself to a surface and or surface variation on the contact surface with the wearer. As described hereinafter, this uniform regional compliance is provided, in part, by the sectional properties or features associated with a region on the compliant tissue interface element.

The compliant tissue interface element comprises a fluidly-sealed foamed silicone rubber layer. The term "fluidly sealed" refers to a foamed silicone rubber layer that precludes air from transmitting through the compliant tissue interface element for a period of time required for normal use of the chamber. By way of example, a latex balloon is "fluidly sealed" to helium if normal use of the balloon is for 6 hours, despite the fact that over time that helium may ultimately leak from the balloon, and despite the fact that the balloon may burst if put under abnormal conditions.

In certain embodiments, the sealing element of the invention provides a contact interface of a negative pressure therapy device configured to conform to a continuous contact area on the individual at the external area of the neck approximately corresponding to the anterior triangle of the neck. The term "approximately corresponding to" an anatomical location refers to contacting closely to the actual location, shape or size but perhaps not necessarily completely, accurately or exactly.

Most preferably, the sealing element is configured to follow the contour of the therapy device which is designed to approximately conform to an individual from approximately a first location corresponding to a first gonion on one side of the individuals mandibular body to a second location corresponding to the individuals mental protuberance to a third location corresponding to the second gonion on the opposite side of the individual's mandibular body and a fourth location corresponding to the individuals thyroid cartilage further configured to return to approximately the first location corresponding to the first gonion.

The gonion, as used herein, describes the approximate location on each side of the lower jaw on an individual at the mandibular angle. The mandibular protuberance, as used herein, describes the approximate location of the chin, the center of which may be depressed but raised on either side forming the mental tubercles. The thyroid cartilage, as used herein, describes the approximate location of the large cartilage of the larynx in humans.

The sealing element and chamber element are designed to create uniform contact pressure onto the tissue of the user when a therapeutic level of pressure is applied. The sealing element is preferably a perpendicular width (wide and narrow) and thickness to achieve the desired contact pressure properties. The perpendicular width component is the total width of the sealing, from the tip of the outside edge of the sealing element through the root and to the tip of the inside edge of the sealing element. The width of sealing element may vary along the peripheral axis of the contact area of the sealing element to accommodate for station load variations due to non-uniform shape of the therapy device that contains a chamber that is oval in shape and further contains a central bend to accommodate the mating surface on the neck of the patient corresponding to approximately the upper airway and maintain a constant contact pressure of the negative pressure therapy device.

In various embodiments of the sealing element, locations on the flange element of the device may be substantially wider than other locations. In one aspect the total flange width may vary from approximately 28.0 millimeters to approximately 17.0 millimeters. "Substantially wider" as used herein refers to an increase in width of at least about 10%, more preferably at least about 20%, and still more preferably at least about 30% or more from one location to another, for example in an embodiment of the invention the width of the flange element at the fourth location corresponding to approximately the middle of the neck of the user is approximately 39% wider than the first and third locations that corresponding to the mandible and gonion regions of the user. Wider sections may be found in regions where a larger load displacement is needed for example at the second and fourth locations and narrower sections may be found in regions where smaller load displacement is needed for example at the first and third locations on the user.

The thickness of the flange element may also vary along the perpendicular width along the circumference of contact surface of the therapy device to accommodate for anatomical variation and varying vacuum cross section. As used herein, thick or thin, describes the distance between the surface of the flange contacting the individual and the (distal) surface of the flange element contacting the chamber element of the vacuum chamber of a negative pressure therapy device. The thickness of the flange element at the root may vary from approximately 4.5 millimeters to 1.0 millimeters at the inside of the root and 3.0 millimeters to 1.2 millimeters at the outside of the root. For example, the thickness of the flange element at the junction at the first and third locations on the user may be about 1.6 millimeters inside the root and 2.10 millimeters outside the root.

In certain aspects, locations on the flange element of the device may vary in thickness such that some portions are substantially thicker than others. For example, locations of the flange element may vary in thickness such that one location is substantially thicker than another. As used herein, "substantially thicker" refers to an increase in thickness of at least about 20%, more preferably at least about 30%, and still more preferably at least about 50% or more. For example, in an embodiment of the invention the thickness at approximately the second location is approximately 64% thicker that the first and third locations and the first and third locations are approximately 30% thicker than the fourth location.

The thickness of the flange element may further taper outwardly from the root location to a final flange thickness of approximately 0.7 millimeters to approximately 0.1 millimeters. The taper may begin at the root continuing to the inside or outside edge of the flange or the taper may also begin at points about 10%, 15%, 20%, 25%, 30%, 35%, 40%, 45%, 50%, 55%, 60%, 65%, 70%, 75%, 80%, 85%, 90% or 95% away from the tip of the flange element and continue to the inside or outside edge of the flange element to a desired final thickness of approximately 0.7-0.1 millimeters. The taper of the flange at its inner and outer edges assisting in the elimination of edge effects, allowing for minimized tissue irritation and damage. As used herein, "edge effects" refer to the irritation, (redness, swelling) of tissue caused by prolonged contact pressure of a sharp edge on the tissue. The tapering of edges provides for a more flexible and softer edge of the flange The chamber element is stiff along its length and the flange will not appreciably deflect longitudinally. Therefore in addressing the dynamic shape of the target therapy area, regions of the therapy device contain accommodating design features, for example, the variations in the width and thickness of the flange element, and or the addition of the compliant conforming interface that are designed to minimize high pressure points and eliminate contact pressure variations of the therapy device along its contact surface when placed on the user and a therapeutic level of negative pressure is applied.

In regions where the flange contacts a substantially flat surface of the user, the chamber element and flange element can act as an "I-beam" where the force exhibited by the flange on the user is a more linear downward force and cantilever-like. The flange element inside and outside the root point of the chamber element flex according to the thickness of material with the tapered ends of the flange element flexing the most creating a soft transition on the tissue of the user eliminating edge effects as above. As used herein cantilever-like forces are a measurement of the downward force of the chamber divided by the area of the flange at a given point. By way of example, in regions where the flange element lays flat across the tissue, cantilever forces can be balanced by altering the width and thickness of the flange, for example where there is a high vacuum cross section and where larger load distribution is desired (ie. lower contact pressure), a flange with a larger perpendicular width may be utilized and similarly in regions where a smaller load distribution is desired (ie higher contact pressure) a flange with a smaller perpendicular width may be utilized The thickness dimensions of the flange element can give the flange element properties such that in portions of the device, if the flange element is too thin, though it may be very flexible it will have little to no load distributing properties, can bottom out creating point(s) of high contact pressure from the root of the chamber element resulting in leaks and/or discomfort. If the flange element is too thick it will affect its ability to change direction for example be unable to conform to the acute change from the surface of the neck over the mandible toward the ear for example and further allow for an undesirable level of sheer or lateral movement. In a similar fashion, if the width of the flange element is too small it can create a point(s) of high pressure and too wide it may create unnecessary bulk affecting fit and effective therapy area. Transition in widths taper gradually and the aspect ratio minimizes positional instability and optimizes flexibility.

In regions where the flange contacts a curved surface of the user, for example around the chin and over the mandible, the forces observed contain an additional hoop-like force component as the flange bends around those features. "Hoop-like forces" as used herein describe the distribution of force exerted circumferentially, for example, as the flange element travels around location four of the user, the curvature adds additional stiffness to the flange inside and outside the root of the chamber element. In these regions where the added force component of hoop loads exists, the thickness of the flange element may be decreased and the perpendicular width of the flange element may be increased to effectively distribute the load of the chamber and minimize contact pressure variation from station to station when a therapeutic level of negative pressure is applied.

The term "contact pressure" as used herein refers to a pressure imparted on the surface of the tissue by the contact surface of the device. Its value can depend on the vacuum present as well as the structural characteristics of the flange such as the perpendicular width and surface area of the contact surface, and can vary at different locations on the flange.

A larger "perpendicular width" of a contact surface (meaning the direction that is perpendicular to the longest axis of the contact surface, which longest axis may be curved) will have a lower overall contact pressure under the same vacuum pressure as a contact surface with a smaller perpendicular width due to the increased surface area at that particular station of the contact surface. Therefore, in regions where the dome station pressure load is low, the contact surface of the flange can be designed to be of a smaller perpendicular width to effectively increase and "balance" the contact pressure and in regions where the dome station pressure is high, the contact surface of the flange can be designed to be of a larger perpendicular width to effectively decrease and balance the contact pressure where the dome station load is high.

In certain embodiments the location of the chamber element on the flange element (the root location) may vary from the mid-point, inward or outward to further aid in equalizing the contact pressure of the therapy device on the user when a therapeutic level of negative pressure is applied creating and maintaining the balance point of the flange element on the user. For example, movement of the root of the edge of chamber element on the flange element outward from the mid-point of the flange element effectively increases the vacuum cross section and therefore effective contact pressure of the therapy device at that point when a therapeutic level of negative pressure is applied. Movement of the edge of the chamber inward has an opposing effect, providing a larger portion of the flange exposed outside the root location and therapy area decreasing the vacuum cross section. In regions where higher contact pressure is needed, for example where the device approaches the ear of the user, the chamber location can be biased on the flange toward the outer edge increasing the vacuum cross section and effective contact pressure at that point.

The chamber is operably connected to an air pump to produce the therapeutic level of negative pressure within the chamber element. The air pump can be of any type suitable to produce the therapeutic level of negative pressure, for example positive displacement pumps, impulse pumps, velocity pumps, etc which can include manual squeeze bulbs, rotary pumps, lobe pumps, oscillatory pumps etc. In certain embodiments the air pump comprises a piezoelectric material configured to provide an oscillatory pumping action wherein the oscillatory pumping motion operates at a frequency greater that 500 Hz.

The air pump may be a separate component connected to the chamber via a hose or tube or may be configured integrally to the chamber. The air pump can be connected to the chamber element in any suitable fashion, for example an air pump may be externally located outside of the chamber element and connected via a hose or tube, e.g. a stationary bed-side pump, or the pump may be integral to chamber, be battery powered, and wearable by the patient. In certain wearable aspects, the air pump is configured to be integral to the chamber. For example, the air pump may be configured to insert into a sealable aperture on the chamber, the air pump tightly fitting through the aperture creating a seal. As used herein a sealable aperture is an opening through an element of the apparatus that can be closed or sealed from one side or the other with another element of the apparatus creating an air-tight or water tight seal.

In certain embodiments, together or with one or more of the foregoing, a material, which will act as an adhesive layer between the flange element of the therapy device and the user, is applied to the outer contact surface of the flange element. The purpose of the adhesive layer is to provide a sealing, cushioning and/or sheer absorbing (i.e. abrasion resistant) element to the flange element. As used herein sheer refers to sheer strain which is a deformation of a material in which parallel surfaces can slide past one another, for example the contact surface of the flange element and the tissue of the user.

The adhesive layer further must preferentially adhere to the outer contact surface of the negative pressure therapy device and provide a sufficient level of "tack" such that a releasable mechanical anchoring of the therapy device to the tissue of the user is achieved. Tack, as used herein, refers to a material property at the interface created between the adhesive layer and the device, and the tissue of the user at the other interface created between the user and the device.

The adhesive layer may be applied to the contact surface area of the negative pressure therapy device in any suitable method including but not limited to spraying, painting, placing, etc., in single or multiple layers to achieve the desired cushioning and sealing properties including but not limited to thickness, hardness and tack for example. In additional embodiments the adhesive layer may be single layer of a uniform thickness or a single layer of a non-uniform thickness covering the contact surface of the negative pressure therapy device. In further embodiments the adhesive layer may contain a series of parallel adhesive beads spanning the circumference of the contact surface of the negative pressure therapy device wherein the beads can be of a uniform or non-uniform thickness and of a like or varying adhesive and or gel-like material to achieve the desired cushioning and sealing properties.

In certain embodiments an adhesive layer is present on the contact surface of the negative pressure therapy device at a thickness falling within a range of approximately 0.005-0.060 inches. In certain embodiments the adhesive layer is present on the contact surface of the negative pressure therapy device at a thickness falling within a range of approximately 0.010-0.050 inches. In further embodiments the adhesive layer is present on the contact surface of the negative pressure therapy device at a thickness falling within a range of approximately 0.020-0.040 inches.

The adhesive layer may be achieved by using various materials, such as, but not limited to gel, elastomer, viscous solutions, foams and materials of the like. These materials can be of any chemical composition which provides the necessary end use properties (i.e. tack, firmness, medical clearance, etc.). These materials include, but are not limited to polyurethanes, silicones, acroylnitrile butadiene styrene (ABS), hydrogels, and the like. In preferred embodiments, the adhesive layer should have a hardness as measured by ASTM-D2240-00 (American Society for Testing Materials) of between 0 and 50, more preferable between 5 and 30 most preferable between 5 and 15. In certain embodiments the adhesive layer is made of a silicone gel material. The silicone can be any organosilicone which yields the desired properties although polydimethylsiloxane (PDMS) is often chosen.

The adhesive layer may be applied directly to the outer contact surface of the flange element to a desired thickness or in combination with one or more primer layer and or one or more primer layers in combination with one or more adhesion or binding promotor layers to create a lamination stack of materials to a desired thickness. As used herein a "primer" is a substance used as a preparatory coating, acting as a joining surface between the contact surface of the negative pressure therapy device and adhesive layer or an adhesion promoting layer and the adhesive layer. Further, an adhesion promoting layer is a substance used as a coating to preferentially adhere the adhesive layer to the contact surface of the negative pressure therapy device and or the primer layer that is applied to the outer surface of the negative pressure therapy device.

By way of example, a primer layer may be applied to the contact surface of the negative pressure therapy device to a thickness of about 0.005 inches, followed by an adhesive promoting layer to a thickness of approximately 0.005 inches, followed by the application of an adhesive layer to a thickness of approximately 0.040 inches achieving a final thickness of approximately 0.050 inches. A primer layer may be applied directly to the outer contact surface of the negative pressure therapy device followed by the application of the adhesive layer directly to the primer to a desired thickness of approximately 0.050 inches. In additional embodiments, an adhesive promoter may be applied to the contact surface of the negative pressure therapy device followed by the application of the adhesive layer to a desired thickness of approximately 0.050 inches.

In certain embodiments the adhesive layer is a gel layer. As used herein a gel layer is a layer of material that can have properties that are mostly liquid however behave like solids due to the cross-linked nature of its structure. The material chosen for the gel layer may be of a certain cohesive pliable consistency so as to mold to and conform to complex shapes for example imperfections in the tissue. As used herein cohesive pliable consistency, elasticity or firmness of the gel layer is defined as the gel layer's ability to flow, mold and stretch and substantially return its original shape when not applied to a surface. The material chosen for the gel layer may also be of a certain tack so as to mechanically secure to the contact area. As used herein tack is defined as the gel's "stickiness" and is the property that allows the immediate formation of a bond on contact with another surface The adhesive layer material must adhere sufficiently to the therapeutic device such that it stays adhered to the device when the device is removed from the user's tissue. Additionally, must have a tack level that is chosen for appropriate performance at the user's tissue interface. That is, at too great a level of tack removal of the device from the tissue can be difficult, painful or injurious. While insufficient tack can allow the device to move during use or allow the seal to the tissue to open thereby losing the vacuum. The level of tack can be measured by a texture analyzer. For example, using a TA.XT plus with a 7 mm radius and 1 inch diameter spherical head the peak adhesion values should be in a range of 200 to 400 grams peak force more preferably 250 to 350 grams peak force and most preferably 275-325 grams peak force.

As discussed above the tack of the adhesive layer is optimized to achieve a releasable but mechanical anchor of the therapy device to the patient. In certain embodiments the contact surface of the flange element is coated with a primer to preferentially anchor the adhesive layer to the negative pressure therapy device over the contact region of the user.

In certain embodiments the adhesive layer is formed from a washable silicone gel such that when washed and allowed to dry, the adhesive layer returns towards an initial tack. In certain embodiments the silicone gel is chosen from a group with properties that can be controlled including, but not limited to: cross sectional thickness, degree of crosslinking (and thereby firmness and tack) and viscosity (so as to be processable under desired conditions. As used herein viscosity is measured in cps referring to centipoise (cps) were 1 cps=0.01 g/cm/s.

In an embodiment of the invention the gel layer is prepared from a two-part platinum cured organosilicone mixture with properties equivalent to a silicone gel base having an uncatalyzed viscosity of about 31,000 cps and a crosslinker having an uncatalyzed viscosity of about 30,500 cps. The final firmness (cps) of the cured gel may be increased by increasing the proportion of the crosslinker in the mixture or decreased by lowering the proportion of the crosslinker in the mix. The tack of the material can be increased by decreasing the proportion of crosslinker in the mixture or decreased by increasing the proportion of crosslinker in the mix. In order to achieve the desired properties using a silicone gel base of 31,000 cps and a crosslinker of 0,500 cps, the ratio of silicone gel base to crosslinker may range (in parts by weight) from about 0.8:1 to about 1:0.8.

In embodiments of the invention the ratio of 31,000 cps silicone gel base to 30,500 cps cross linker may further range from about 1:0.8 to about 1:1. In other embodiments of the invention the ratio of 31,000 cps silicone gel base to 30,500 cps crosslinker may range from about 0.8:1 to about 1:1. And in further embodiments of the invention the ratio of 31,000 cps silicone gel base to 30,500 cps crosslinker may range from about 0.88:1 to about 1:0.88.

By example of the invention the silicone gel base and the crosslinker are mixed in desired ratios and placed under vacuum in order to remove any bubbles in the mixed solution (de-gassing). Following de-gassing, the silicone gel solution is applied to the contact surface of the flange element and allowed to cure. The mixture can achieve full cure in approximately 24 hours at room temperature however in some embodiments a full cure of the silicone gel may be achieved in about 5 minutes by placing the therapy device containing the silicone gel layer at about 150° C. The cure temperature may be adjusted to suit limiting elements of the therapy device, for example lower melting points of other therapy device elements.

In certain embodiments the adhesive layer is made of a hydrogel. Hydrogels are a three-dimensional network of crosslinked hydrophilic polymer chains that can be crosslinked either physically or chemically. In further embodiments the hydrogel layer may be found as a hydrocolloid wherein the colloid particles are hydrophilic polymers dispersed in water.

In certain embodiments the adhesive layer is made of a combination of materials or similar materials with differing mechanical properties for example differing durometers applied side-by side on the outer contact surface of the fluidly sealed chamber. By way of example, a hydrogel material may be applied to the circumference of the center portion of the outer contact surface of the fluidly sealed chamber and a silicone gel material may be applied on either side peripheral to the hydrogel material. In further embodiments where a combination of materials are applied side-by-side on the outer contact surface of the flange element, a silicone gel layer may be applied to the circumference of the center portion of the out contact surface of the fluidly sealed chamber and a hydrogel material may be applied to either side peripheral to the silicone gel material followed by a final application of a silicone gel material peripheral to the hydrogel material.

In certain embodiments, the compliant contact layer is made of a combination of materials applied side-by side on the outer contact surface of the fluidly sealed chamber. By way of example, a hydrogel material may be applied to the circumference of the center portion of the outer contact surface of the fluidly sealed chamber and a silicone gel material may be applied on either side peripheral to the hydrogel material. In further embodiments where a combination of materials are applied side-by-side on the outer contact surface of the flange element, a silicone gel layer may be applied to the circumference of the center portion of the outer contact surface of the fluidly sealed chamber and a hydrogel material may be applied to either side peripheral to the silicone gel material followed by a final application of a silicone gel material peripheral to the hydrogel material.

As used herein, "user compliance" refers to the patient's adherence to the prescribed usage of a therapy device for example the usage of a device throughout a sleep cycle.

As used herein, "device compliance" refers to the ability of the device or elements of the device to accommodate variation, for example, bending, twisting, compressing and or expanding of the device in response to device application and usage including anatomical variations and or movement of the patient.

Aspects of the device may be made of a generally rigid material. The term "generally rigid" as used herein refers to a material which is sufficiently rigid to maintain the integrity of the particular element in question. The skilled artisan will understand that a number of polymers may be used including thermoplastics, some thermosets, and elastomers. Thermoplastic materials become flowing liquids when heated and solids when cooled, they are often capable of undergoing multiple heating/cooling cycles without losing mechanical properties. Thermoset materials are made of prepolymers which upon reaction cure irreversibly into a solid polymer network. Elastomers are viscoelastic materials which exhibit both elastic and viscous properties and can be either a thermoplastic or thermoset. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

Aspects of the device may be formed using a number of methods known to those of skill in the art, including but not limited to injection molding, machining, etching, 3D printing, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold—in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

Example 1

Material preparation was done using a 10 Shore A durometer liquid silicone rubber (Silbione® LSR 4310, Elkem Silicones USA) and an ammonium bicarbonate foaming agent (Med4-4900, Nusil Technology LLC). The liquid silicone rubber used is a two component platinum-catalyzed silicone elastomer that was manually mixed in a 1:1 ratio. The ammonium bicarbonate was measured out at 1.5% by weight of the liquid silicone rubber mixture, then combined and manually blended together with it.

Material forming was done using a knife coating machine. Knife coating is a process by which a thin liquid coating is formed on a continuous polymer web substrate by the application of an excess of coating liquid that is subsequently metered by a rigid knife held in close proximity to the rigidly supported web as the web advances. The thickness of the coating depends primarily on the clearance or gap between the knife and the web, and upon the geometry of the gap (bevel angle, length, etc.). In this embodiment, an excess of the liquid silicone rubber and ammonium bicarbonate mixture described above was applied to the advancing web, upstream of a knife that was set to a gap of 2.16 mm clearance. As the web advanced, the metered 2.16 mm thickness portion of the web was exposed to 150° C. heat intended to simultaneously activate the foaming and cure the liquid silicone rubber. Heating was maintained for a minimum period of 5 minutes, during which time the ammonium bicarbonate foaming caused the material to swell in thickness. After the 5 minute heating period, the cured elastomeric foam was allowed to return to room temperature where the resultant foam thickness settled to a nominal 3.05 mm.

Material application was accomplished by die cutting the elastomeric foam sheet into an appropriate 2-dimensional shape (i.e. roughly a 114 mm×190 mm oval donut having a 25 mm wide annulus) that corresponded with the 3-dimensional shape of the tissue contacting flange of a negative pressure appliance. Once die cut into shape, the polymer web backing was removed from the backside of the elastomeric foam donut and a uniform thin coating of silicone rubber adhesive (Sil-Poxy®, Smooth-On, Inc. was manually applied in its place along the entire annulus. The coated elastomeric foam donut was subsequently manually manipulated to align and press it into place on the tissue contacting flange of the negative pressure appliance. The silicone rubber adhesive was allowed to cure at room temperature for a minimum of 12 minutes.

The end result was a negative pressure appliance with an elastomeric foam that continuously conformed with its tissue contacting flange.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims:

What is claimed is:

1. An appliance configured to contact tissue, comprising:
   (a) a tissue interface portion comprising a viscoelastic foam configured to provide a tissue contact surface of the appliance, wherein the viscoelastic foam comprises each of the following properties:
      a Shore 000 of between 1 and 40, as measured using the Standard Test Method for Rubber Property-Durometer Hardness ASTM D2240-15;
      a density (specific gravity) of between about 0.2 to 0.7 g/cm$^3$; and/or
      a level of tack of between about 0.2 and about 9 mJ/cm$^2$ as measured using the Standard Test Method for Pressure-Sensitive Tack of Adhesives ASTM D2979-16;
      an elastic (storage) modulus of between about 1 kPa and about 15 kPa;
      a viscous (loss) modulus of between about 0.8 kPa and about 7 kPa; and
   (b) a non-contacting portion configured to support the tissue interface portion and to be separated from the tissue by the tissue interface portion.

2. An appliance according to claim 1, wherein the viscoelastic foam comprises one or both of an elastic (storage) modulus of between about 10 kPa and about 15 kPa and a viscous (loss) modulus of between about 2 kPa and about 7 kPa.

3. An appliance according to claim 1, wherein the appliance further comprises a second tissue contact surface that is not a viscoelastic foam.

4. An appliance according to claim 1, wherein the viscoelastic foam does not include a tackifier or an adhesive and wherein the tack is an inherent property of the viscoelastic foam.

5. An appliance according to claim 1, wherein the viscoelastic foam exhibits a tack of at least about 0.5 mJ/cm$^2$.

6. An appliance according to claim 1, wherein the viscoelastic foam provides an air leakage past the sealed surface of no more than about 8 mL/min at atmospheric pressure.

7. An appliance according to claim 1, wherein the viscoelastic foam provides an air leakage past the sealed surface of no more than about 0.8 mL/min at atmospheric pressure.

8. An appliance according to claim 1, wherein the viscoelastic foam provides a seal to the tissue, and an air leakage past the seal of no more than about 0.008 mL/min at atmospheric pressure.

9. An appliance according to claim 1, wherein the viscoelastic foam has a density of about 0.5 g/cm$^3$ or less.

10. An appliance according to claim 1, wherein the viscoelastic foam is a foamed silicone rubber.

11. An appliance according to claim 1, wherein the viscoelastic foam comprises a reinforcing filler.

12. An appliance according to claim 11, wherein the reinforcing filler is selected from the group consisting of silica, silica aerogel, silica xerogel, titanium dioxide, diatomaceous earth, iron oxide, aluminum oxide, zinc oxide, quartz, calcium, carbonate, magnesium oxide, carbon black, graphite, glass fibers, glass micro spheres, glass micro balloons, glass beads, carbon fibers, silicon carbide, polystyrene beads, microcrystalline cellulose, nanoparticles and metal fibers.

13. An appliance according to claim 1, wherein the viscoelastic foam comprises an antimicrobial agent.

14. An appliance according to claim 13, wherein the antimicrobial agent comprises one or more agents selected from the group consisting of silver salts, silver ions, silver ions encapsulated in a glass particle, silver sodium zirconium hydrogenphosphate, 3-(Trimethoxysilyl)propyl dimethyl octadecyl ammonium chloride, benzalkonium chloride, polyhexamethylenebiguanide (PHMB) and chlorhexidine.

15. An appliance according to claim 1, wherein the appliance is an eye protection mask, a SCUBA mask, a swim goggle, a medical appliance, a breathing mask a set of headphones, ear plugs, ear buds, earphones, a catheter, a vascular stent, a vascular graft, a vascular stent-graft.

16. An appliance according to claim 1, wherein the medical appliance is a negative pressure chamber configured to cover tissue of a human or animal body.

17. An appliance according to claim 16, wherein the medical appliance is a negative-pressure wound therapy device or a continuous negative external pressure (cNEP) therapy device for maintenance of airway patency by the application of an external negative pressure to tissue overlying a portion of a human airway.

* * * * *